(12) United States Patent
Meltola et al.

(10) Patent No.: US 7,763,439 B2
(45) Date of Patent: *Jul. 27, 2010

(54) TWO-PHOTON ABSORBING DIPYRROMETHENEBORON DIFLUORIDE DYES AND THEIR APPLICATIONS

(75) Inventors: Niko Meltola, Piispanristi (FI); Aleksi Soini, Lieto (FI)

(73) Assignee: Arctic Diagnostics Oy, Turku (FI)

( * ) Notice: Subject to any disclaimer, the term of this patent is extended or adjusted under 35 U.S.C. 154(b) by 1132 days.

This patent is subject to a terminal disclaimer.

(21) Appl. No.: 10/482,205

(22) PCT Filed: Jul. 1, 2002

(86) PCT No.: PCT/FI02/00586

§ 371 (c)(1),
(2), (4) Date: Dec. 29, 2003

(87) PCT Pub. No.: WO03/005030

PCT Pub. Date: Jan. 16, 2003

(65) Prior Publication Data

US 2004/0157231 A1 Aug. 12, 2004

Related U.S. Application Data

(60) Provisional application No. 60/301,788, filed on Jul. 2, 2001.

(30) Foreign Application Priority Data

Jul. 2, 2001 (FI) .................................. 20011439

(51) Int. Cl.
G01N 33/53 (2006.01)
G01N 33/533 (2006.01)
G01N 33/543 (2006.01)
G01N 21/76 (2006.01)
C07K 1/10 (2006.01)
C07K 1/04 (2006.01)

(52) U.S. Cl. ...................... 435/7.92; 436/546; 436/518; 436/172; 530/402; 530/403

(58) Field of Classification Search ................ 436/546, 436/518, 56, 172, 800; 435/7.92, 7.93, 7.1; 548/405

See application file for complete search history.

(56) References Cited

U.S. PATENT DOCUMENTS 4,489,165 A 12/1984 Wagner et al. .............. 436/500

(Continued)

FOREIGN PATENT DOCUMENTS

WO WO 93/09185 5/1993

(Continued)

OTHER PUBLICATIONS

STN International, File Chemcats, AN 2000:175375, http://www/probes.com/handbook/print/0104.html.

(Continued)

*Primary Examiner*—Shafiqul Haq
(74) *Attorney, Agent, or Firm*—James C. Lydon

(57) ABSTRACT

A separation free bioanalytical assay method for measuring an analyte from a biological fluid or suspension containing microparticles as a bioaffinity binding solid phase, a biospecific secondary reagent labelled with a two-photon fluorescent dipyrromethene boron difluoride dye of specified structure, focusing the laser into the reaction suspension, and measuring two-photon excited fluorescence from single microparticles when they randomly float or are guided by the radiation pressure of the excitation laser through the focal volume of the laser beam.

3 Claims, 11 Drawing Sheets

Compound 7

Compound 8

Compound 9

U.S. PATENT DOCUMENTS

| | | | | |
|---|---|---|---|---|
| 5,274,113 A | * | 12/1993 | Kang et al. | 548/405 |
| 5,512,486 A | | 4/1996 | Giese et al. | 436/63 |
| 5,869,689 A | | 2/1999 | Zhang et al. | 548/405 |
| 5,958,783 A | | 9/1999 | Josel et al. | 436/84 |
| 6,342,397 B1 | * | 1/2002 | Soini et al. | 436/518 |

FOREIGN PATENT DOCUMENTS

| | | |
|---|---|---|
| WO | WO 95/06877 | 3/1995 |
| WO | WO 96/22531 | 7/1996 |
| WO | WO 97/39326 | 10/1997 |
| WO | WO 98/25143 | 6/1998 |
| WO | WO 99/11813 | 3/1999 |
| WO | WO 99/63344 | 12/1999 |

OTHER PUBLICATIONS

Wories et al., "A Novel Water-soluble Fluorescent Probe," 104 *Recl. Trav. Chim. Pays-BAs*, 288-291 (1985).

Hänninen et al., A New Microvolume Technique for Bioaffinity Assays Using Two Photon Excitation, 18 *Nature Biotechnology* 548-550 (2000).

* cited by examiner

Compound 1

Compound 2

Compound 3

Compound 4

Compound 5

Compound 6

Compound 7

Compound 8

Compound 9

Compound 10

Compound 11

Compound 12

Compound 13

Compound 14

Compound 15

Compound 16

Compound 17

TWO-PHOTON ABSORBING DIPYRROMETHENEBORON DIFLUORIDE DYES AND THEIR APPLICATIONS

This application is a U.S. National Stage of International application PCT/FI02/00586, filed Jul. 1, 2002, and which claims priority of U.S. provisional application No. 60/301,788, filed Jul. 2, 2001 and Finnish patent application 20011439, filed Jul. 2, 2001.

FIELD OF THE INVENTION

Present invention relates to dipyrrometheneboron difluoride dyes and to the use of these dyes under two-photon excitation. In addition the present invention relates to the use of dipyrrometheneboron difluoride dyes and their conjugates in bioanalytical assays that are based on two-photon excitation.

BACKGROUND OF THE INVENTION

The publications and other materials used herein to illuminate the background of the invention, and in particular, cases to provide additional details respecting the practice, are incorporated by reference.

Dipyrrometheneboron difluoride dyes

The dipyrrometheneboron difluoride dyes have been first described by Treibs and Kreuzer, *Liebigs Ann. Chem.* 718 (1968) 208 and by Wories H. J. et al., *Recl. Trav. Chim. Pays-Bas* 104 (1985) 288. Since then dipyrrometheneboron difluoride dyes have found various applications. Dipyrrometheneboron difluoride dyes exhibit strong fluorescence at visible region of spectrum. Dipyrrometheneboron difluoride dyes have the following general properties: High quantum efficiency, sharp absorption and emission bands and high absorption coefficient. A wide variety of dipyrrometheneboron difluoride dyes are commercially available today (Haugland R. P., Handbook of Fluorescent Probes and Research Chemicals, 6$^{th}$ ed, Molecular Probes, Eugene, Oreg., 1996). Syntheses and fluorescence properties of different derivatives of these dyes have been described in publications and patents. U.S. Pat. Nos. 4,916,711, 5,189,029, 5,446,157 and EP 0 361 936 by Morgan and Boyer describe the use of dipyrrometheneboron difluoride dyes in photodynamic therapy (PDT) and in production of laser light. According to Morgan and Boyer dipyrrometheneboron difluoride dyes have a low triplet-triplet absorption that together with low laser action threshold enables the production of a laser beam with an intensity higher than by using conventional laser dyes. Moreover the high photostability of these dyes results in reduced degradation of the dye material.

Fluorescent dyes are widely used as tracers for localisation of biological structures by fluorescence microscopy, for quantitation of analytes by fluorescence immunoassay, for flow cytometric analysis of cells and for many other applications. Usually these fluorescent dyes are attached to biomolecules via a covalent linkage. For this attachment (labelling) these dyes need a functional group that can be reacted with another functional group in a biomolecule. Commonly used reactive functional groups include reactive carboxylic acid esters, acid anhydrides, hydrazines and isothiocyanates. U.S. Pat. No. 4,774,339 describes the use of dipyrrometheneboron difluoride dyes as fluorescent labels. According to U.S. Pat. No. 4,774,339 the fluorescence properties dipyrrometheneboron difluoride dyes are not sensitive to solvent or pH. These dyes have also narrow absorption and emission bandwidths, high quantum yield and high photostability.

The basic chromophore (I) of dipyrrometheneboron difluoride dye has absorption and emission maxima around 500 nm.

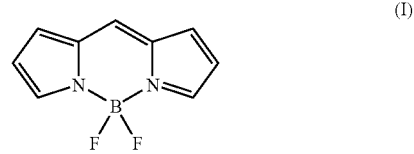

(I)

Basic Chromophore of Dipyrrometheneboron Difluoride Dye

The absorption and emission wavelengths of the dipyrrometheneboron difluoride dyes can usually be altered by changing the substituents of the chromophore. Lengthening of the π-electron conjugation leads to the shift of the emission and absorption bands to longer wavelengths. Lengthening of the π-electron conjugation affects also photostability, solubility and fluorescence quantum yield. U.S. Pat. Nos. 5,274,113, 5,451,663 and WO 93/09185 describe dipyrrometheneboron difluoride labelling reagents that have an absorption maxima between 525 nm and 650 nm. This shift in absorption and emission wavelengths has been achieved by adding an unsaturated organic group into the chromophore. The patents describe the use of aryl, heteroaryl and alkenyl substituents for lengthening of the π-electron conjugation pathway. U.S. Pat. No. 5,248,782 describes heteroaryl substituted dipyrrometheneboron difluoride dyes and U.S. Pat. No. 5,187,288 describes ethenyl substituted dipyrrometheneboron difluoride dyes that have absorption maxima between 550 nm and 670 nm. The shift in absorption and emission wavelengths was in most cases accompanied with an increased absorption coefficient and photostability. The lengthening of the π-electron conjugation pathway was also described by Chen J. et al., *J. Org. Chem.*, 65 (2000) 2900. Chen J. et al. describe aryl substituted dipyrrometheneboron difluoride dyes that have absorption maxima between 620 and 660 nm and fluorescence emission between 630 and 680 nm. U.S. Pat. No. 5,433,896 describes dipyrrometheneboron difluoride dyes that contain fused aryl substituents. These dibenzopyrromethene boron difluoride dyes have absorption and emission maxima between 600 nm and 740 nm. The molar absorption coefficient of these dyes were most often above 100 000 cm$^{-1}$M$^{-1}$.

Wories H. J. et al., Recl. Trav. Chim. Pays-Bas 104 (1985) 28 describe a method for introducing sulfonic acid groups to dipyrrometheneboron difluoride dyes and thus increase hydrophilicity of these dyes. They report mono- and disulfonated dipyrrometheneboron difluoride dyes that have absorption maxima at 495 nm and 491 nm, and emission maxima at 515 and 510 nm.

The dipyrrometheneboron difluoride dyes have found various applications as fluorescent labels. The synthesis and versatility of these dyes has been reported in publications and patents referred to above. Most of these dyes however suffer from intrinsic hydrophobicity that limits their use for fluorescent labelling of biomolecules. That is the case especially with dipyrrometheneboron difluoride dyes that contain aryl substituents.

The dipyrrometheneboron difluoride dyes can be used not only as fluorescent markers but also as laser dyes and as probes in photodynamic therapy for treatment of tumours. These dyes have also found applications in staining of microparticles (U.S. Pat. No. 5,723,218) and as optical recording media (U.S. Pat. No. 6,060,606).

Two-Photon Excitation

In 1931 Maria Göppert-Mayer (*Ann. Phys.* 9 (1931) 273) postulated that a molecule can simultaneously absorb two photons. This phenomenon remained for a long time without practical use until the intensive laser light sources became available. Two-photon excitation is created when, by focusing an intensive light source, the density of photons per unit volume and per unit time becomes high enough for two photons to be simultaneously absorbed into the same chromophore. The absorbed energy is the sum of the energies of the two photons. The probability of two-photon excitation is dependent on the $2^{nd}$ power of photon density. The absorption of two photons is thus a non-linear process of the second order. The simultaneous absorption of two-photons by one chromophore yields to a chromophore in excited state. This excited state can be relaxed by emission of a photon of higher energy than photons of the illuminating laser. In this context the process that includes two-photon excitation and subsequent radiative relaxation is called two-photon fluorescence. Two-photon fluorescence has usually similar spectral properties to those of one-photon excited fluorescence of the same chromophore (Xu C. and Webb W. W., *J. Opt. Soc. Am. B,* 13 (1996) 481). The molecules, which can be excited with two simultaneously absorbed photons and the excited state relaxation is accompanied with fluorescence emission, are in this context called two-photon fluorescent dyes.

One of the key features of two-photon excitation is that excitation takes place only in the clearly restricted 3-dimensional (3D) vicinity of the focal point. The outcome of this feature is high 3D spatial localization of the generated fluorescence emission. Due to the non-linear nature of excitation, minimal background fluorescence outside the focal point, in the surroundings of the sample and in the optics, is generated. Another key feature of two-photon excitation is that illumination and emission takes place in essentially different wavelength ranges. A consequence of this property is that leakage of scattered illumination light into the detection channel can be easily attenuated by using low-pass filters (attenuation of at least 10 orders of magnitude). Since the excitation volume is very small, two-photon excitation is most suitable for observation of small sample volumes and structures.

The intrinsic properties of two-photon excitation, low-background and small excitation volume, suggest that two-photon excitation is best suited for applications requiring fluorescence detection from small volumes. In fact the two-photon excitation volume is in the range of femtoliters or even below, depending on the optical parameters of the system. In such a small excitation volume only a few fluorescent molecules are present at any given time point. One of the inherent features that relate to two-photon excitation techniques is the low absorption cross-section of fluorophores. Another feature is that two-photon excitation is usually performed with pulsed lasers, the time in-between pulses with conventional lasers is longer than the lifetime of fluorophores leading to a reduced excitation rate. These features together with small excitation volume results in relatively low signal level. Another problem relates to the intense illumination intensity that can cause unexpected effects. These effects can be categorized in two different types: cumulative multiple pulse effect (accumulation of energy) and single pulse effect (direct non-linear absorption of second or higher order). The cumulative multiple pulse effect is particularly relevant when using pulsed lasers with high repetition rate (sub-picosecond pulsed lasers with repetition rate in the order of 100 MHz). Under such high repetition rate it is possible that the energy is accumulated to the long lifetime triplet states of the dye molecule. The triplet states are usually non-radiative and thus accumulation of the energy to these states decreases the two-photon fluorescence yield. The two-photon excitation efficiency ($Ex_{2ph}$) is proportional to the peak power ($P_p$) and the pulse duration ($\tau_{pulse}$) of the laser light ($EX_{2ph} \propto P_p^2 * \tau_{pulse}$). According to this, using pulsed lasers with high peak power and moderate repetition rate (picosecond to nanosecond pulsed lasers with kHz repetition rate) leads to high two-photon excitation efficiency. The high two-photon excitation efficiency in this context means that almost all of the dye molecules at the focal point of the laser beam are excited by a single laser pulse. FIG. 1 represents the two-photon excitations of the dye molecules vs. illumination intensity. In an ideal case the emission vs. illumination intensity curve co-insides with the two-photon excitations vs. illumination intensity curve. Usually that is the case when the illumination intensity is clearly below the intensity that is required for reaching the saturation level (A, FIG. 1) and the two-photon excited fluorescence thus follows the quadratic dependence of the illumination intensity. At (C, FIG. 1) or near (B, FIG. 1) saturation level (when using high two-photon excitation efficiency laser in order to maximise the two-photon excited fluorescence) the single pulse effect becomes particularly relevant. In such a case the excited state absorption and stimulated emission may decrease the two-photon fluorescence yield and cause deviations from the quadratic dependence of the emission relative to illumination intensity. Depending on the sample the appearance of these effects may limit the maximum usable illumination intensity.

Ehrlich J. E. et al. *Opt. Lett.* 22 (1997) 1843, Baur J. W. et al., *Chem. Mater.* 11 (1999) 2899 and Kim O.-K. et al. *Chem. Mater.* 12 (2000) 284 have reported that the two-photon absorption coefficients can vary significantly depending on the measurement conditions such as intensity level and pulse duration of the laser beam. It has been pointed out that when very intense laser illumination is used for measuring the two-photon absorption cross-section or two-photon fluorescence yield, some linear processes may play a role. Such phenomenon like excited state absorption has been proposed to be a reason for quenching of some fluorophores under two-photon excitation (Fischer A. et al., *Appl. Opt.* 34 (1995) 1989).

Xu C. and Webb W. W., *J. Opt. Soc. Am. B,* 13 (1996) 481 reported two-photon absorption cross-sections of various fluorescent dyes including a dipyrromethenboron difluoride dye described by Wories H. J. et al., *Recl. Trav. Chim. Pays-Bas* 104 (1985) 288. The dipyrromethenboron difluoride dye studied by Xu and Webb has one-photon absorption maximum at 495 nm and emission maximum at 515 nm. Two-photon excitation spectra were recorded between 690 and 1050 nm. In this study the light source was a Ti:Sapphire laser with a nominal pulse length of 80 femtoseconds. According to Xu and Webb the two-photon absorption cross-section of the dipyrromethenboron difluoride dye is approximately one order of magnitude lower than that of Rhodamine B. Xu and Webb did not report any observations of quenching of Rhodamine B under high intensity laser illumination or any deviations from the quadratic dependence of the emission relative to illumination intensity. However, quenching of Rhodamine B was reported earlier by Fischer A. et al., *Appl. Opt.* 34 (1995) 1989. According to Fischer et al. the quenching effect in two-photon excitation leads to poorer three-dimensional resolution in two-photon microscopy.

Bioanalytical Applications of Two-Photon Excited Fluorescence

Fluorescence has found various applications in the field of bioanalytics. Applications such as immunoassays, DNA-hybridisation assays and receptor binding assays using fluorescence as a detection method have been introduced during the last three decades. These assays utilise specific bioaffinity reactions in determination of the analyte amount in a sample. The amount of analyte can be determined by monitoring the fluorescence signal that depends on the amount of bound analyte. These assays can also be based on monitoring of the change on the fluorescence properties upon specific binding reaction. This change in fluorescence property can be either change in fluorescence intensity, change in emission wavelength, change in decay time or change in fluorescence polarisation.

Immunoassays have been used extensively in clinical diagnostics for determination of certain diseases or physiological condition. Immunoassays can be categorised to two different types of assays, competitive and non-competitive assays. In the competitive method, the labelled antigen (secondary biospecific reagent) competes with the analyte to bind to a limited quantity of antibody (primary biospecific reagent). The concentration of analyte can be determined from the proportion of the labelled antigen bound to the antibody or from the proportion of the free fraction of the labelled antigen. In a non-competitive method (immunometric method) the analyte is bound to an excess amount of binding antibody (primary biospecific reagent). An excess of labelled antibody (secondary biospecific reagent) binds to another site of the analyte. The amount of analyte can be determined on basis of the fraction of the labelled antibody bound to the analyte. The assay methods can also be divided to heterogeneous and to homogeneous (separation free) methods. Separation of the bound and free fractions is necessary in heterogeneous assays but not in homogeneous assays [Miyai K., *Principles and Practice of Immunoassay*, (ed. Price C. P. and Newman D. J.) Stockton Press, New York 1991, 246 and Hemmila I. A., *Applications of Fluorescence in Immunoassays*, (ed. Winefordner J. D.) John Wiley & Sons, New York 1991].

One of the early reports relative to analytical applications of two-photon excitation was published by Sepaniak et al., *Anal. Chem.*, 49 (1977) 1554. They discussed the possibility of using two-photon fluorescence excitation for HPLC detection. Low background and simplicity of the system were demonstrated.

The usefulness of two-photon fluorescence excitation in laser scanning microscopy was first demonstrated by Denk et al., *Science*, 248 (1990) 73. They used a mode-locked dye laser providing a stream of femtosecond pulses at a repetition rate of 80 MHz. The advent of Ti:sapphire lasers facilitated the implementation of two-photon excitation in a standard laser scanning fluorescence microscope. Two-photon fluorescence excitation has been extensively discussed in the literature during the last ten years. Many research contributions have been published that are related to two-photon excited fluorescence-imaging technology. The development has also lead to industrial manufacture of two-photon laser scanning microscope systems.

Lakowicz et al., *J. Biomolec. Screening* 4 (1999) 355 have shown that the time dependent intensity decays of DAPI (4,6-diaminidino-2-phenylindole) bound to DNA and calcium-dependent fluorophores can be measured with two-photon fluorescence excitation. Lakowicz et al. reported the use of multiphoton excitation in high throughput screening applications. They have shown that two-photon-induced fluorescence of fluorescein can be reliably measured in high-density multiwell plates.

Most of the bioanalytical applications of two-photon excited fluorescence that are described in the literature relate to two-photon imaging microscopy (Denk W. et al. U.S. Pat. No. 5,034,613, Denk W. et al., *Science* 248 (1990) 73. The use of two-photon fluorescence excitation in laser scanning microscopy provides inherent 3D spatial resolution without the use of pinholes, a necessity in confocal microscopy. With a simple optical design two-photon excitation microscopy provides comparable 3D spatial resolution with that of ordinary one-photon excited confocal microscopy. The disadvantage of the two-photon excitation technology is the need of an expensive laser capable of generating intense ultra short pulses with a high repetition frequency.

The recent development of less expensive laser technology is very encouraging in regard to usefulness of two-photon fluorescence excitation technology in routine bioanalytical applications (Hänninen P. et al., *Nat. Biotechnol.* 18 (2000) 548; Soini J. T. et al. *Single Mol.* 1 (2000) 203; WO 98/25143 and WO 99/63344). According to WO 98/25143 and WO 99/63344 instead of expensive mode-locked photon excitation. These lasers are monolithic, small, simple and low in cost. WO 98/25143 and WO 99/63344 describe the use of two-photon excitation in bioanalytical assay method. This bioanalytical assay method can be used for analytes in solution or in a biological suspension and it employs microparticles as a bioaffinity binding solid phase to which a primary biospecific reagent is bound. This bioanalytical assay method utilises a biospecific secondary reagent that is labelled with a two-photon fluorescent dye. According to WO 98/25143 and WO 99/63344 contacting the microparticles with the analyte and the biospecific secondary reagent in the reaction volume and the use of fluorescence detection that is based on two-photon excitation enables a separation free assay method. The amount of the analyte bound to the primary biospecific reagent and to the microparticles is detected by the two-photon excited fluorescence signal originating from the labelled secondary biospecific reagent. The labelled secondary biospecific reagent can bind either to the analyte (non-competitive, immunometric method) or to the primary biospecific reagent (competitive method). The primary and secondary biospecific reagents are biologically active molecules, such as haptens, biologically active ligands, drugs, peptides, oligonucleotides, nucleotides, nucleic acids, polypeptides, proteins, antibodies, or fragments of antibodies. According to WO 98/25143 and WO 99/63344 a laser with high two-photon excitation efficiency is focused into the reaction suspension and two-photon excited fluorescence is measured from single microparticles when they float through the focal volume of the laser beam. Alternatively the microparticles can be trapped for a period of fluorescence detection with an optical trap, which is brought about with a laser beam. The trapping of microparticles to the focal point of the laser beam is based on optical pressure that is generated onto the microparticle by the illuminating laser. According to WO 98/25143 optical trapping increases the duration of the particle at the focal point of the laser beam and decreases the dead time of the measurement. According to WO 98/25143 optical trapping requires relatively high laser average power and illumination intensity. In this case the average power of the laser determines the efficiency of trapping. The repetition rate of the microchip laser is relatively low and thus it is necessary to use high pulse energy and consequently a high peak power of the illuminating laser in order to obtain the average power of the laser that is sufficient for optical trapping. The use of high peak power, and a laser with high two-photon excitation efficiency may lead to reduction in the two-photon excited fluorescence yield and may also reduce the signal-to-background ratio in separation free assays because of the single pulse effect. In practise, however, it is often reasonable to use a laser with as high as possible two-photon excitation efficiency in order to maximise the fluorescence signal.

OBJECT AND SUMMARY OF THE INVENTION

The object of the invention is to provide an improved separation free bioanalytical assay method for measuring an analyte from a biological fluid or suspension.

This invention concerns a separation free bioanalytical assay method for measuring an analyte from a biological fluid or suspension comprising of microparticles as a bioaffinity binding solid phase, a biospecific secondary reagent labelled with a two-photon fluorescent dye, focusing the laser into the reaction suspension, measuring two-photon excited fluorescence from single microparticles when they randomly float or are guided by the radiation pressure of the excitation laser through the focal volume of the laser beam. The two-photon fluorescent dye has a structure (II):

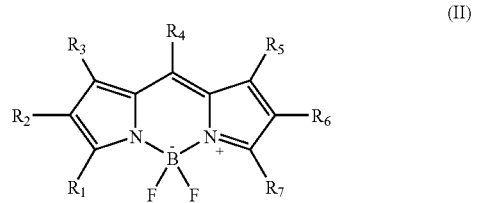

(II)

Either at least one of groups $R_1$, $R_2$, $R_3$, $R_4$, $R_5$, $R_6$ or $R_7$ is a substituted or unsubstituted phenyl, thienyl, pyrrolyl, furanyl, oxazolyl, isoxazolyl, oxadiazolyl, imidazolyl, benzoxazolyl, benzothiazolyl, benzimidazolyl, benzofuranyl, indolyl, conjugated ethenyl, dienyl or trienyl group, and at least one of the groups $R_1$, $R_2$, $R_3$, $R_4$, $R_5$, $R_6$ or $R_7$ is substituted to yield a chemically reactive group that can be used for selective covalent linkage to other molecules, and at least one of the groups $R_1$, $R_2$, $R_3$, $R_4$, $R_5$, $R_6$ or $R_7$ is substituted to yield a water-solubilizing group, and the remaining groups of $R_1$, $R_2$, $R_3$, $R_4$, $R_5$, $R_6$ and $R_7$ are each independently selected from the group consisting of hydrogen, halogen, alkyl, cyano, carboxy, each of which can optionally be substituted; or groups $R_1$, $R_2$, $R_3$, $R_5$, $R_6$ and $R_7$ are substituted or unsubstituted alkyl groups, $R_4$ is a hydrogen, or substituted or unsubstituted alkyl, and at least one of the groups $R_1$, $R_2$, $R_3$, $R_4$, $R_5$, $R_6$ or $R_7$ is substituted to yield a chemically reactive group that can be used for selective covalent linkage to other molecules and at least one of the groups $R_1$, $R_2$, $R_3$, $R_4$, $R_5$, $R_6$ or $R_7$ is substituted to yield a water-solubilizing group.

DETAILED DESCRIPTION OF THE INVENTION

Figure 1:
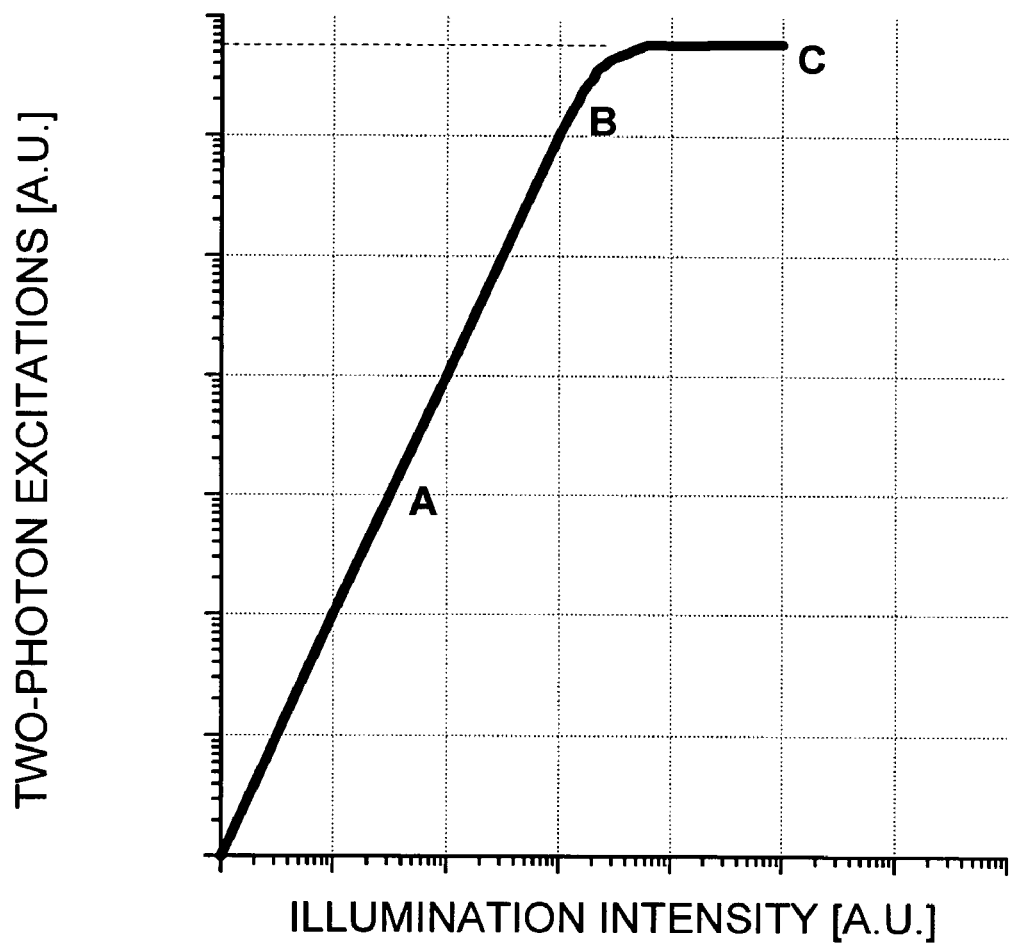
FIG. 1 is a plot of two-photon excitations vs. illumination intensity.

Terms used in this application can be defined as follows:

Two-photon fluorescence: Process that includes simultaneous absorption of two photons into the same chromophore and subsequent radiative relaxation of the excited state.

Two-photon fluorescent dye: Molecules, which can be excited with two simultaneously absorbed photons and the excited state relaxation is accompanied with fluorescence emission.

Cumulative multiple pulse effect: Effect that results from accumulation of excitation energy to long lifetime triplet states. This effect causes decrease of the fluorescence yield when using sub-picosecond lasers with a repetition rate in the order of 100 MHz for two-photon excitation. This effect causes deviation from the quadratic dependence of the two-photon fluorescence vs. illumination intensity before reaching the saturation level of the dye.

Single pulse effect: Effect that results from direct nonlinear absorption of second or higher order. This effect causes decrease of the fluorescence yield when using lasers with high pulse peak power ($P_p$) and picosecond to nanosecond nominal pulse length ($\tau_{pulse}$) with kHz repetition rate for two-photon excitation. This effect causes deviation from the quadratic dependence of the two-photon fluorescence vs. illumination intensity before reaching the saturation level of the dye.

Two-photon excitation efficiency: Number of excitations per time unit. Two-photon excitation efficiency ($Ex_{2ph}$) is proportional to the peak power ($P_p$) and the pulse duration ($\tau_{pulse}$) of the laser light ($Ex_{2ph} \propto P_p^2 * \tau_{pulse}$).

Laser with high two-photon excitation efficiency: Laser that is capable of exciting the two-photon fluorescent dye close to saturation level (B, FIG. 1).

Signal-to-background ratio: The ratio between the signal obtained from the dye on the particle surface and the signal obtained from the dye in solution.

Illumination intensity: Laser pulse peak power per beam cross-section area unit.

Average power: The laser beam energy emitted in one second.

Microparticle: A spherical or non-spherical solid object, which can be used as a solid phase carrier for chemical or biochemical species. Microparticles are generally considered to be of 0.01-100 μm in diameter and may be composed of polymer, glass, silica or other material.

The present invention is related to two-photon absorbing fluorophores that have high two-photon excited fluorescence yields and that exhibit exceptionally low quenching by the single pulse effect even under high intensity laser illumination. This invention offers two-photon fluorescent dyes that can be used in a separation free bioanalytical assay method based on the use of a laser with high two-photon excitation efficiency. The dipyrrometheneboron difluoride dyes and the conjugates of the said dyes, which are the object of the present invention, have been found to provide exceptionally high two-photon excited fluorescence yields. The two-photon fluorescent dipyrrometheneboron difluoride dyes and the conjugates of the said dyes that are the object of the present invention, are ideally suited for a microparticle based bioanalytical assay system because the dipyrrometheneboron difluoride dyes and the conjugates of the said dyes exhibit exceptionally low quenching by the single pulse effect even under the high average power of a laser that is required for the optical trapping of the microparticles. The present invention introduces novel two-photon fluorescent dipyrrometheneboron difluoride dyes that are especially suitable for labelling of biomolecules. These two-photon fluorescent dipyrrometheneboron difluoride dyes are hydrophilic in nature and soluble in aqueous solutions. Solubility of these dyes in aqueous solutions makes them ideally suitable to be used in bioanalytical assay methods.

Figure 2A:
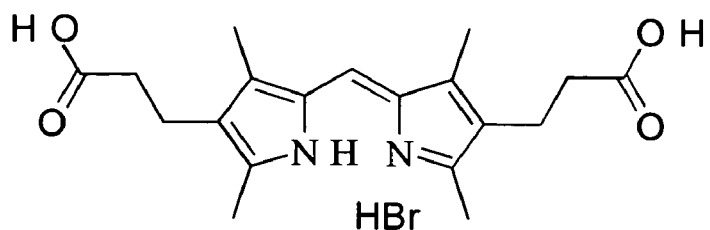
FIG. 2a presents alkyl substituted dipyrrometheneboron difluoride dyes.
Figure 2A:
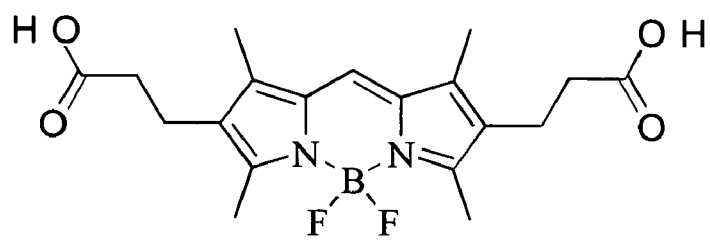
Figure 2A:
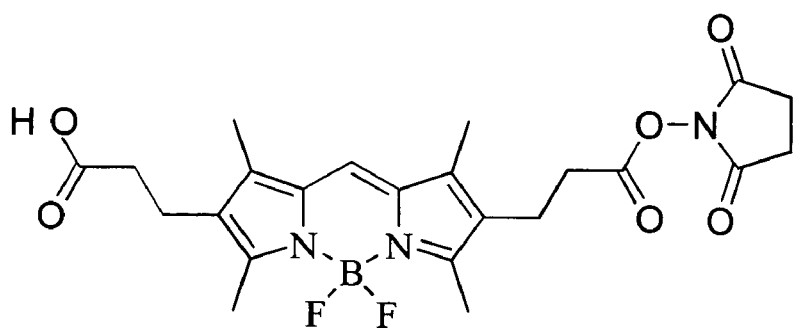
Figure 2B:
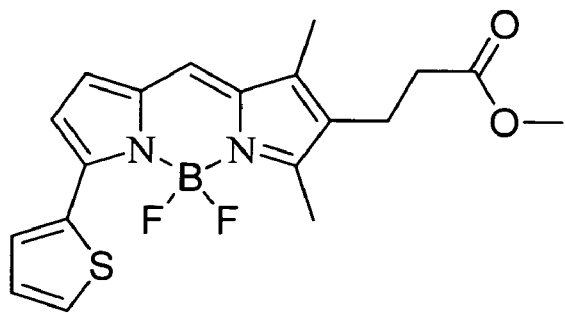
FIGS. 2b and 2c present heteroaryl substituted dipyrrometheneboron difluoride dyes.
Figure 2B:
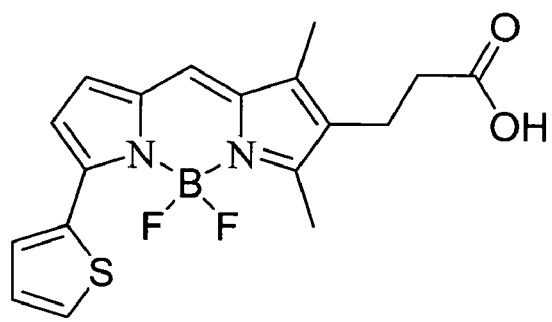
Figure 2B:
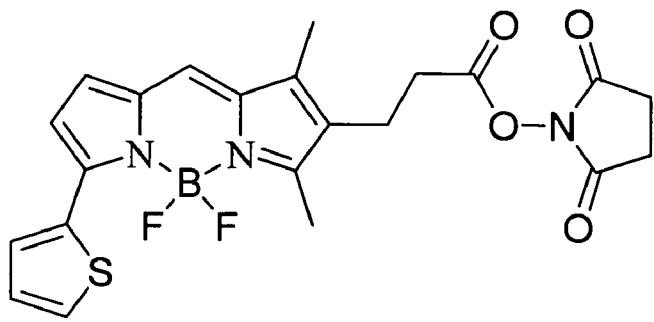
Figure 2C:
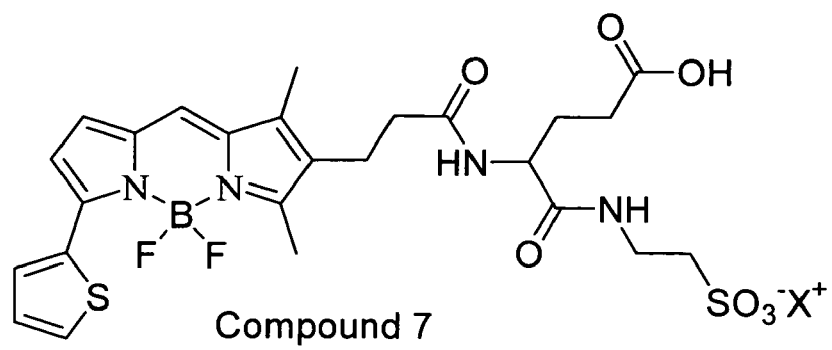
Figure 2C:
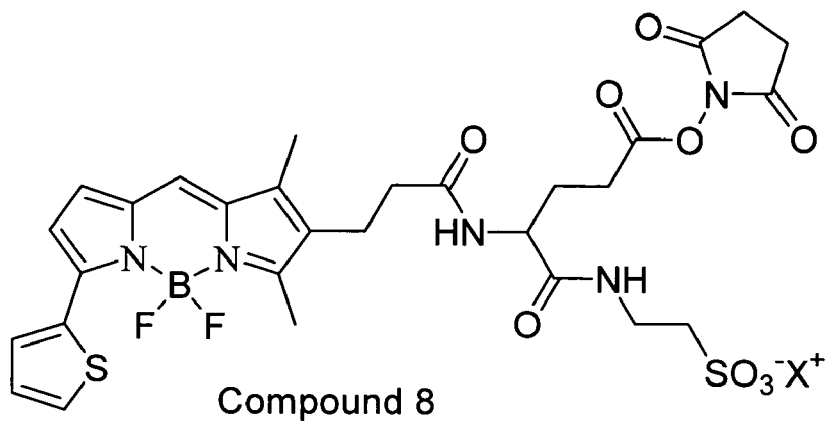
Figure 2C:
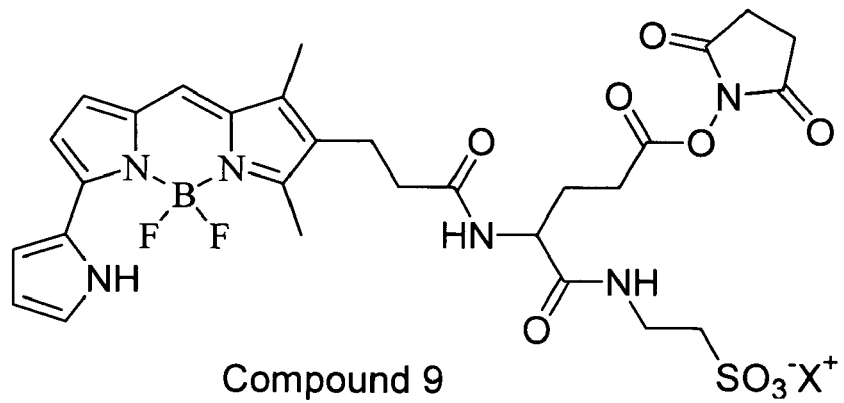
Figure 2D:
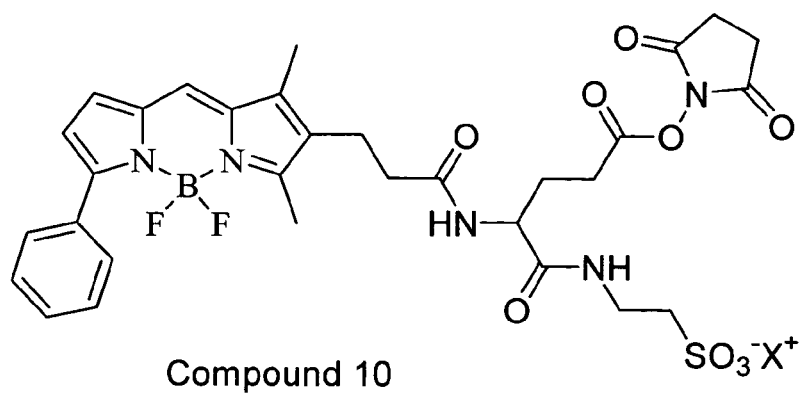
FIG. 2d presents aryl substituted dipyrrometheneboron difluoride dyes.
Figure 2D:
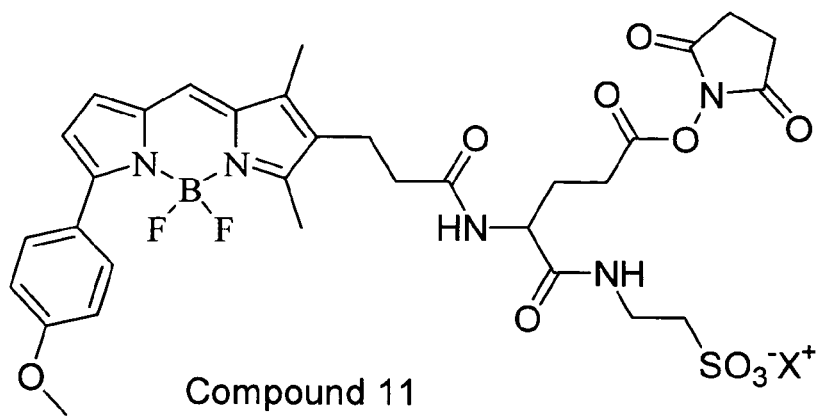
Figure 2E:
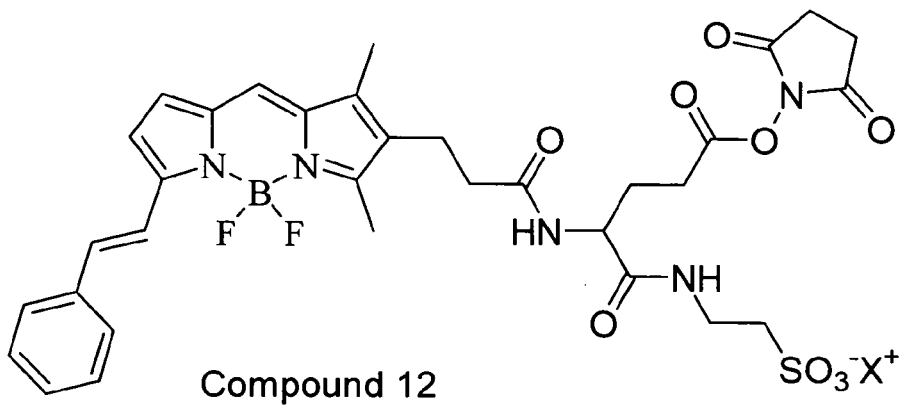
FIGS. 2e and 2f present phenylethenyl substituted dipyrrometheneboron difluoride dyes.
Figure 2F:
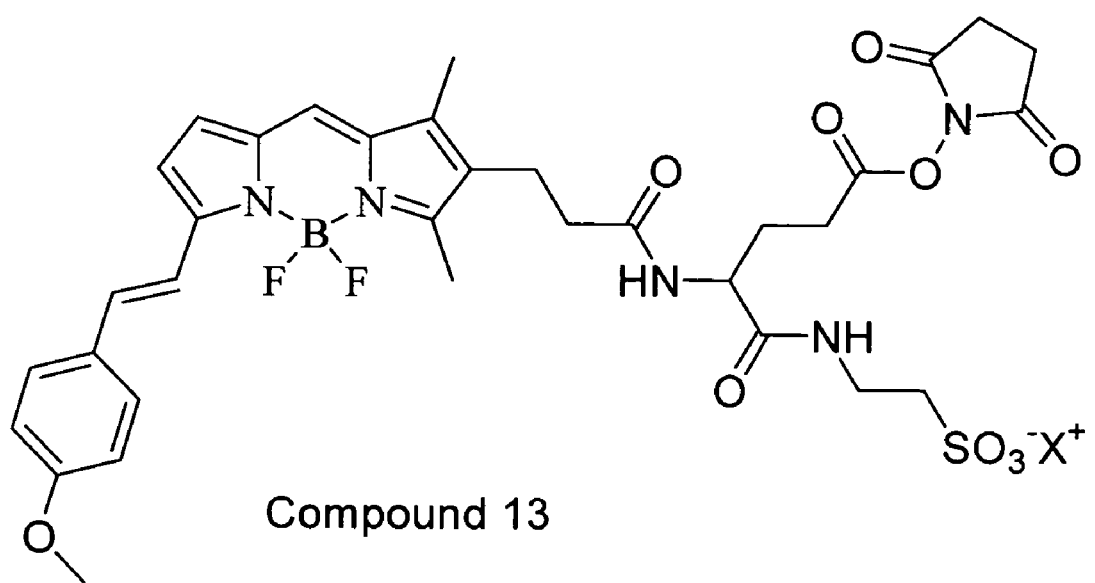
Figure 2G:
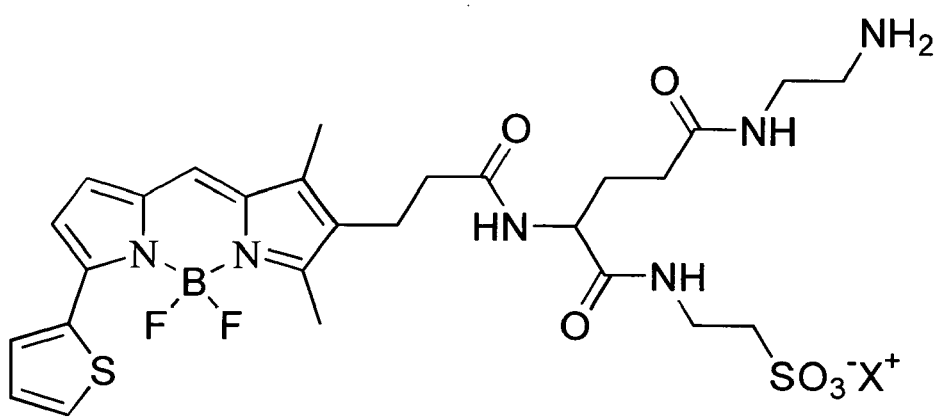
FIGS. 2g and 2h present thienyl substituted dipyrrometheneboron difluoride dyes with different reactive groups.
Figure 2G:
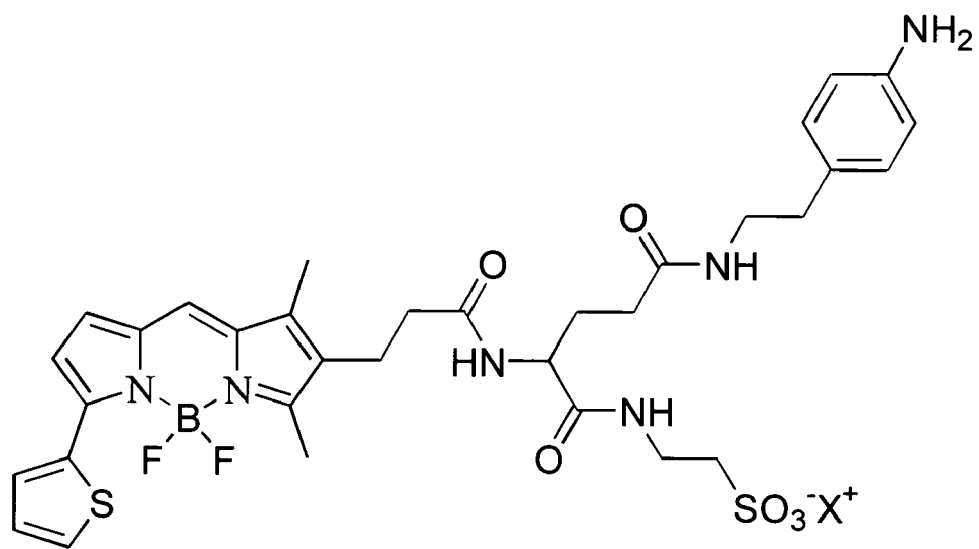
Figure 2H:
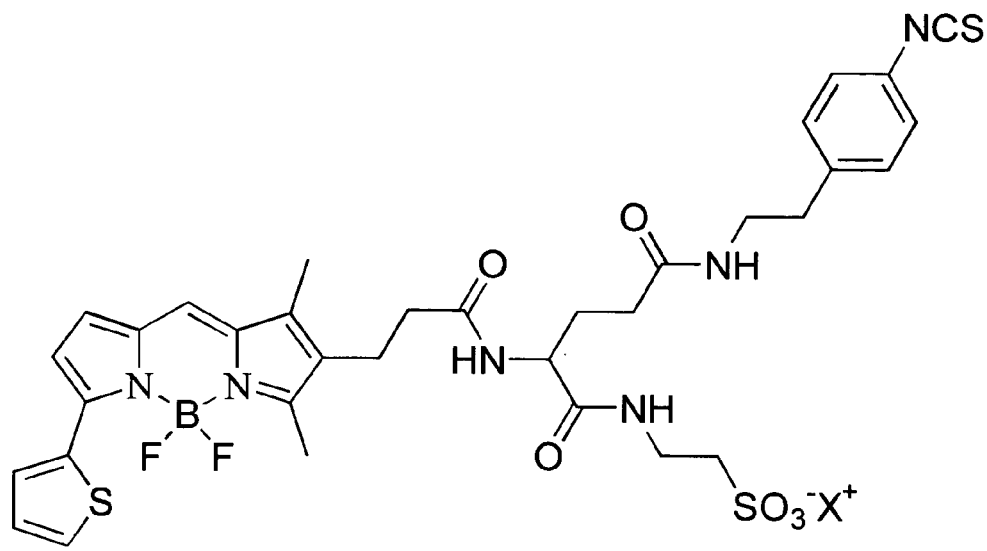
Figure 2H:
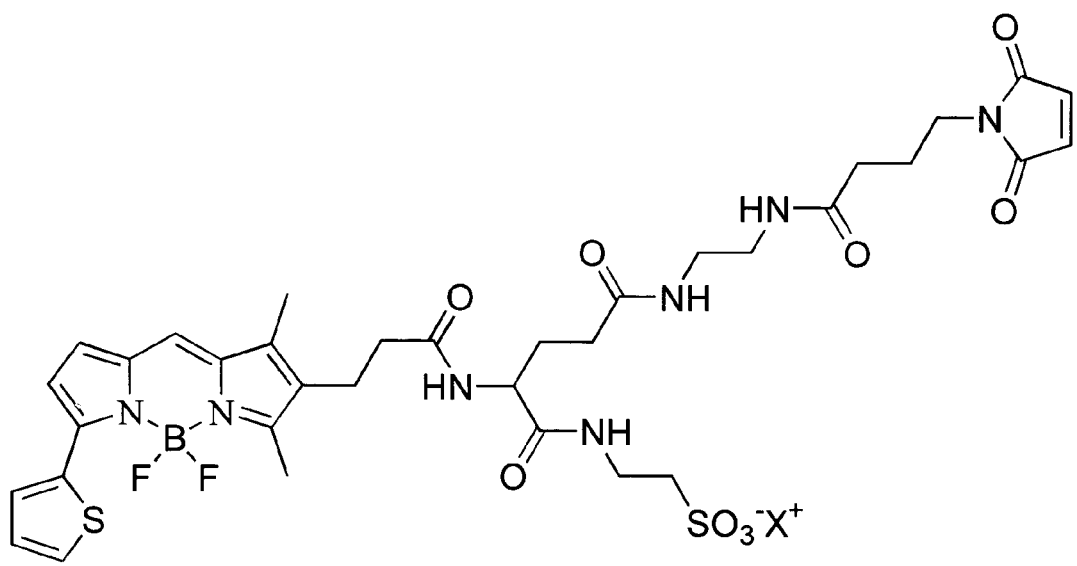
Figure 3:
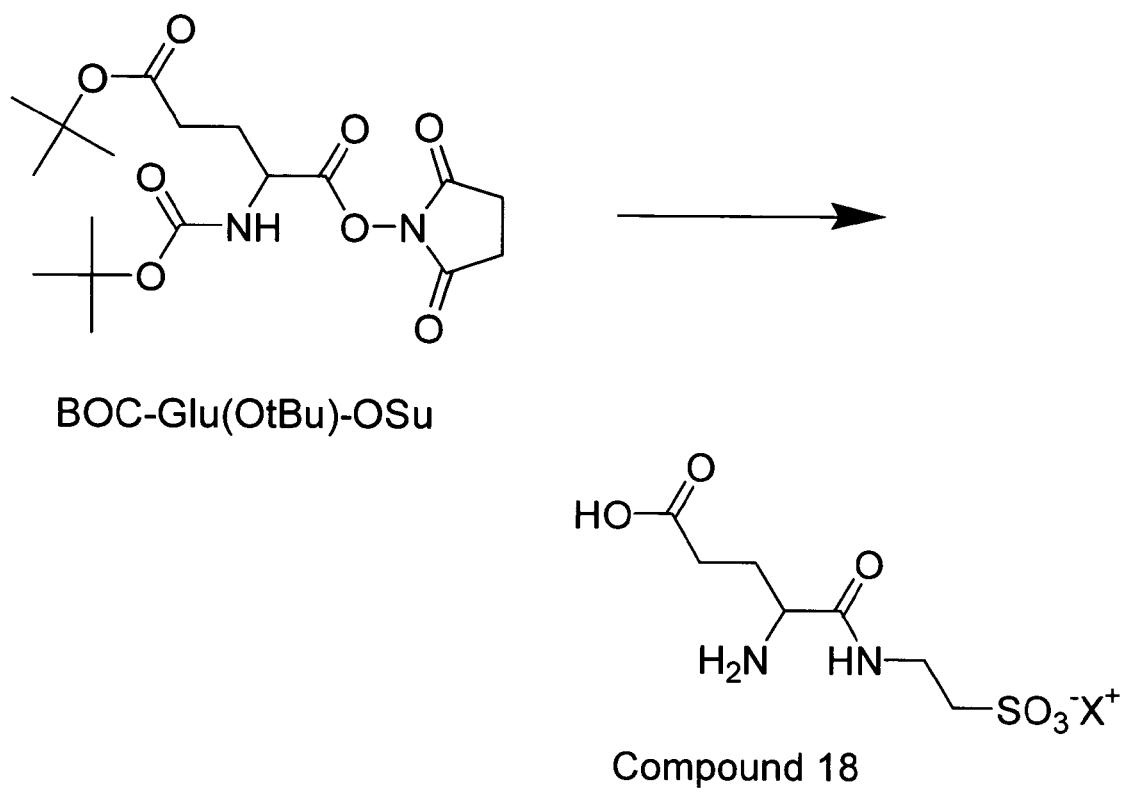
FIG. 3 presents a linker compound.
Figure 4:
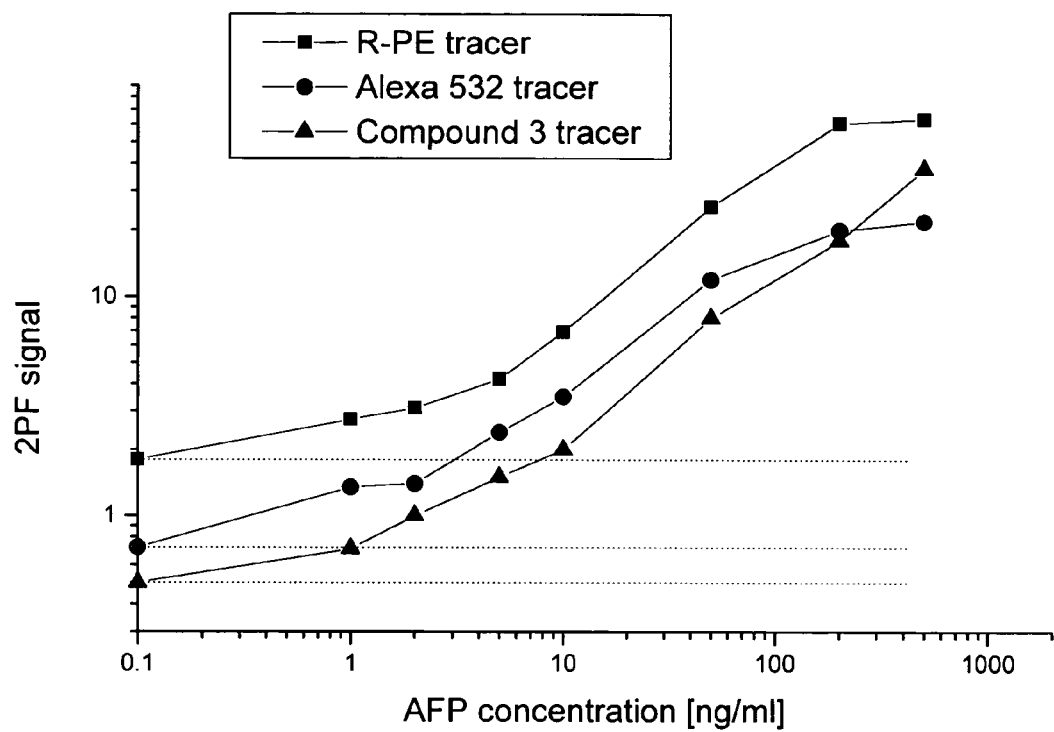
FIG. 4 is a plot of two-photon fluorescence signal vs. analyte (AFP) concentration in an immunoassay.
Figure 5:
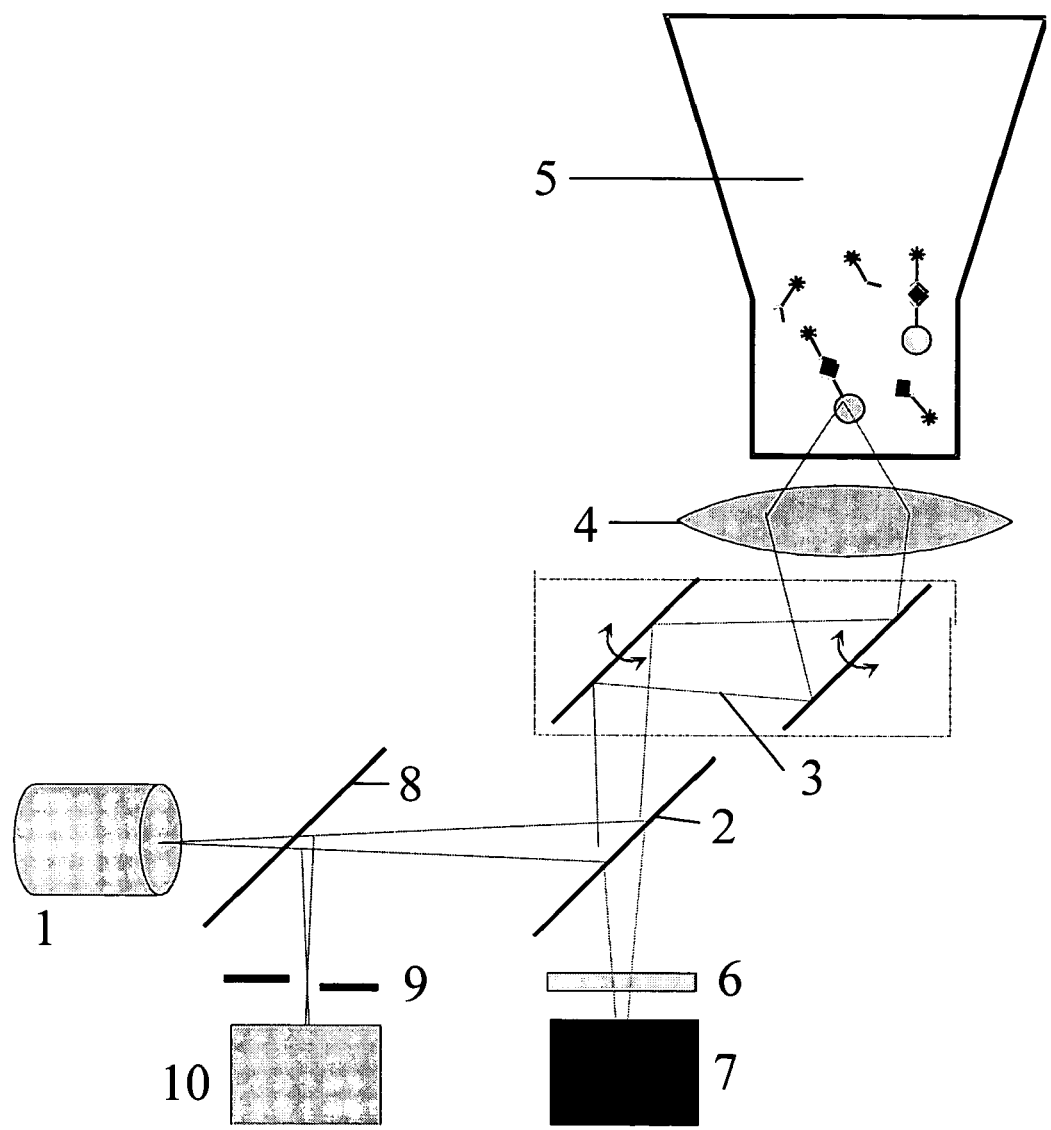
FIG. 5 is an optical scheme of the instrument used in two-photon fluorescence measurements.

FIG. 1 is a plot of two-photon excitations vs. illumination intensity. At low illumination intensities (A) excitation follows a quadratic dependence of the illumination intensity. In order to maximise the two-photon excited fluorescence a dye should be excited close to saturation level (B). At saturation level (C) almost all of the dye molecules become excited. FIG. 2a present alkyl substituted dipyrrometheneboron difluoride dyes described in examples 1-3 as compounds 1-3. FIGS. 2b and 2c present heteroaryl substituted dipyrrometheneboron difluoride dyes described in examples 4-9 as compounds 4-9. $X^+$ is a cationic counterion. FIG. 2d presents phenyl substituted dipyrrometheneboron difluoride dyes described in examples 10 and 11 as compounds 10 and 11. $X^+$ is a cationic counterion. FIGS. 2e and 2f present phenylethenyl substituted dipyrromethene-boron difluoride dyes described in examples 12 and 13 as compounds 12 and 13. $X^+$ is a cationic counterion. FIGS. 2g and 2h present thienyl substituted dipyrrometheneboron difluoride dyes with amino-, arylamino-, maleimide- and isothiocyanate reactive groups described in examples 14-17 as compounds 14-17. $X^+$ is a cationic counterion. FIG. 3 presents a linker compound 18 that is used to increase solubility of the dyes in aqueous solutions. $X^+$ is a cationic counter-ion. FIG. 4 is a plot of two-photon fluorescence signal vs. analyte (AFP) concentration in an immunoassay based on two-photon fluorescence as described in example 21. The AFP concentration 0 ng/ml is presented as a concentration of 0.1 ng/ml because of the logarithmic scale used in FIG. 4. FIG. 5 is an optical scheme of the instrument used in two-photon fluorescence measurements. A passively Q-switched Nd:YAG microchip laser 1 is used as an illumination source for two-photon excited fluorescence. The wavelength of the laser is 1064 nm, the pulse duration is 1 ns and the repetition rate is 20 kHz. The naturally diverging laser light beam is directed with a dichroich mirror 2 through an optical scanner unit 3 to the entrance aperture of the objective lens 4. The illumination at the entrance aperture is gaussian filling about 70% of the full aperture. The objective lens then focuses the illumination light into a special cuvette 5 that has a thin optical bottom (thickness 0.2 mm). The average optical output power reaching the sample is 50 mW. The size of the focal volume is about 1 femtoliter. The two-photon excited fluorescence signal in the range 540-700 nm is collected from the full aperture of the objective lens 4 and directed through the dichroich mirror 2 and the band pass filter 6 to the photomultiplier tube 7. In case of particle measurements, both the two-photon excited fluorescence light and the microparticle back-scattered (reflected) laser light are measured. The dichroich mirror 2 and the 2% beam splitting window 8 deflect the back-scattered light to the pinhole 9 making the detection of the scattering signal confocal. The detector for the scattering signal is a near infrared GaAs pin photodiode 10. The particles are continuously tracked by using a three-dimensional beam scanner 3. The xy-scanner is optomechanical and is positioned as close to the entrance aperture of the objective lens as possible. Due to the partial illumination of the objective entrance aperture the deflection of the beam at the full deflection angles of the xy-scanners does not cause significant cutting of the beam by the aperture edges. When the amplitude of the back scattering signal exceeds a preset threshold level, it indicates that a microparticle appears in the vicinity of the focal volume and the x- and y-scanner mirrors are stopped. Optical pressure caused by the illuminating laser beam traps the particle and guides it through the centre of laser beam focus. The fluorescence signal is measured while the particle is in focus i.e. the back scattering signal exceeds the preset threshold. In addition to xy-scanning a further z-scanning movement is performed by moving the objective slowly in the axial direction. The amplitude of this movement is 150 μm and the movement is not stopped for particle measurement. Despite of slow z-scanning the particle remains in the focus on basis of optical trapping forces.

The two-photon fluorescent dyes that are used in combination with lasers with high two-photon excitation efficiency must be selected so that the fluorophore has minimal quenching by single pulse effect. This enables excitation of the fluorophore population close to saturation level and thus maximisation of the two-photon fluorescence signal. Appropriate selection of the fluorescent dye also enables the exploitation of optical trapping of microparticles in bioanalytical assays that are based on two-photon excitation and the use of microparticles as a solid carrier described in WO 98/25143 and WO 99/63344. When high repetition rate lasers are used occurrence of the singlet-triplet crossing also becomes an important parameter for selection of an appropriate fluorophore. With fluorophores that have low singlet-triplet crossing rate the accumulation of energy to the non-radiative triplet states can be avoided. The two-photon fluorescent dipyrrometheneboron difluoride dyes that are the object of the present invention fulfil both two essential requirements. Moreover, the position of the absorption and emission bands of two-photon fluorescent dipyrrometheneboron difluoride dyes can be tuned by appropriate substitution of the basic chromophore. This property is essentially important when tuning the properties of the chromophore suitable for one particular laser. Fluorescence quantum yield of dipyrrometheneboron difluoride dyes is generally above 70%. The high quantum yield together with low quenching rate by single pulse effect offers high two-photon excited fluorescence when using laser with high two-photon excitation efficiency as an illumination source. The two-photon excited fluorescence yields of the dipyrrometheneboron difluoride dyes according to this invention are surprisingly high. Contrary to previously published data [Xu C. and Webb W. W., *J. Opt. Soc. Am. B*, 13 (1996) 481] we have found that the two-photon excited fluorescence yields of the dipyrrometheneboron difluoride dyes are even higher than the two-photon excited fluorescence yield of Rhodamine B. Moreover, the minimal quenching of the two-photon fluorescent dipyrrometheneboron difluoride dyes by single pulse effect enables the exploitation of a laser with high two-photon excitation efficiency as illumination source without significant loss of 3D spatial resolution of the system. Two-photon fluorescent dipyrrometheneboron difluoride dyes can also be modified by appropriate side chain substitution to be used both in aqueous solutions and in organic media.

This invention relates to the bioanalytical assay method described in Hänninen P. et al., *Nat. Biotechnol.* 18 (2000) 548; Soini J. T. et al. *Single Mol.* 1 (2000) 203; WO 98/25143 and WO 99/63344. The present invention offers two-photon fluorescent dyes that in combination with the bioanalytical assay method described in Hanninen P. et al., *Nat. Biotechnol.* 18 (2000) 548; Soini J. T. et al. *Single Mol.* 1 (2000) 203; WO 98/25143 and WO 99/63344 offers high assay performance. The two-photon fluorescent dipyrromethenboron difluoride dyes and the conjugates of the said dyes that are the object of the present invention can be used in a separation free bioanalytical assay method based on the use of a laser with high two-photon excitation efficiency without any significant reduction in signal-to-background ratio.

According to present invention the secondary biospecific reagent is labelled with two-photon fluorescent dipyrromethenboron difluoride dye. The secondary biospecific reagent is a biologically active molecule, such as a hapten, a biologically active ligand, a drug, a peptide, an oligonucleotide, a nucleotide, a nucleic acid, a polypeptide, a protein, an antibody, or a fragment of an antibody. The secondary biospecific reagent labelled with two-photon fluorescent dipyrromethenboron difluoride dye can bind either to the analyte (non-competitive assay) or to the primary biospecific reagent (competitive binding assay). The amount of the analyte bound to the primary biospecific reagent on the microparticles is detected by the two-photon excited fluorescence signal originating from the secondary biospecific reagent that is labelled with two-photon fluorescent dipyrromethenboron difluoride dye.

Optical trapping (described in WO 98/25143), which increases the duration of the particle at the focal point of the laser beam and which decreases the dead time of the measurement, requires relatively high average power of the laser. The high average power with low pulse frequency leads to a high pulse energy that may lead to quenching of the fluorescence by single pulse effect. According to present invention the two-photon fluorescent dipyrromethenboron difluoride dyes are ideally suited for the microparticle based bioanalytical assay system. These dyes exhibit exceptionally low quenching by the single pulse effect even under the high average power of the laser that is required for the optical trapping of the microparticles.

The two-photon fluorescent dipyrromethenboron difluoride dyes and the conjugates of the said dyes that are the object of the present invention can also be used in a separation free bioanalytical assay method that is based on monitoring the two-photon excited fluorescence of the unbound biospecific reagent. The primary biospecific reagent is bound either on the microparticles or on the walls of the cuvette. The secondary biospecific reagent labelled with two-photon fluorescent dipyrromethenboron difluoride dye can bind either to the analyte (non-competitive assay) or to the primary biospecific reagent (competitive binding assay). The amount of the analyte that is bound on the microparticles or on the walls of the cuvette via the primary biospecific reagent is determined on the basis of two-photon excited fluorescence signal originating from the unbound secondary biospecific reagent that is labelled with two-photon fluorescent dipyrromethenboron difluoride dye.

The two-photon fluorescent dipyrromethenboron difluoride dyes that are the object of this invention have the general structure (II) below.

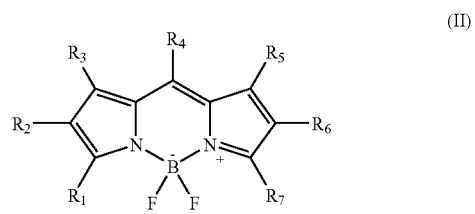

(II)

In this structure, $R_1$, $R_2$, $R_3$, $R_4$, $R_5$, $R_6$ and $R_7$ are chosen among the substituents hydrogen, halogen, alkyl, cycloalkyl, alkenyl, arylalkenyl, aryl, alkylaryl, heteroaryl, acyl, alkoxy, cyano, carboxy, amino, hydroxyl, alkoxycarbonyl, nitro, alkylamino, dialkylamino and sulfo, alone or in combination. Furthermore, the substituents on the chromophore can be further modified to provide a chemically reactive functional group. Chemically reactive groups that can be used for selective covalent linkage to other molecules include but are not limited to derivatives of carboxylic acids, carboxylic acid reactive esters, carboxylic acid anhydrides, maleimides, sulfonyl chlorides, sulfonyl fluorides, hydrazines, amines, alcohols, acyl azides, isocyanates, aldehydes, haloacetamides, triazines or isothiocyanates.

The substituents that can be used for shifting the absorption and emission to longer wavelengths are essentially important when tuning the properties of the basic chromophore suitable for one particular laser. For example, in two-photon excitation with Nd:YAG lasers at a wavelength of 1064 nm the fluorescence emission band should be above 532 nm (sum of the energy of the two 1064 nm photons). A convenient way to shift absorption and emission bands of dipyrromethenboron difluoride basic chromophore to longer wavelengths is to lengthen the π-electron conjugation. This can be done for example by addition of an unsaturated organic group into the basic chromophore. According to this, the preferred compounds of the present invention have a structure where at least one of the substituents $R_1$, $R_2$, $R_3$, $R_4$, $R_5$, $R_6$ and $R_7$ is selected from the group consisting of phenyl, thienyl, pyrrolyl, furanyl, oxazolyl, isoxazolyl, oxadiazolyl, imidazolyl, benzoxazolyl, benzothiazolyl, benzimidazolyl, benzofuranyl, indolyl, conjugated ethenyl, dienyl, trienyl, and any of the aforementioned optionally substituted with one or several substituents. The optional substituents are preferably selected from the group consisting of a halogen, hydroxy, alkoxy, cyano, nitro, carboxy, amino, alkylamino, dialkylamino, sulfo and a straight or branched alkyl, preferably comprising 1 to 10 carbons, that may contain heteroatoms, substituted heteroatoms or heteroatom containing sidechains. The remaining substituents $R_1$, $R_2$, $R_3$, $R_4$, $R_5$, $R_6$ and $R_7$ are each independently selected from the group consisting of hydrogen, halogen, alkoxy, cyano, carboxy alkoxycarbonyl, nitro, alkylamino, dialkylamino, sulfo and a straight or branched alkyl, preferably comprising 1 to 10 carbons that may contain heteroatoms, substituted heteroatoms or heteroatom containing sidechains. Among the most preferred compounds are those where $R_1$ is a substituted or unsubstituted phenyl, thienyl, pyrrolyl or phenylethenyl; $R_2$, $R_3$ and $R_4$ are hydrogens; $R_5$, $R_6$ and $R_7$ are each independently either hydrogen, an alkyl or a substituted alkyl.

A preferred compound according to present invention can also have a structure where at least one of the substituents $R_1$, $R_2$, $R_3$, $R_4$, $R_5$, $R_6$ or $R_7$ is —YZ, where —Y— is a linker unit and Z is a chemically reactive group which can be used for covalent coupling of the chromophore to other molecules, such as biomolecules. The linker unit —Y— is either a covalent bond or a $C_1$-$C_{20}$ straight or branched alkylene, arylene, alkarylene, aralkylene group or a combination of these. The linker unit —Y— may also contain heteroatoms, substituted heteroatoms or heteroatoms containing sidechains, or cyclic residues. The linker unit —Y— may also comprise or be composed of residues of polymers, preferably residues of polymers such as polypeptides, polysaccharides, polynucleotides, polyethers or other. The remaining substituents of $R_1$, $R_2$, $R_3$, $R_4$, $R_5$, $R_6$ and $R_7$ are each independently selected among such substituents as hydrogen, halogen, alkyl, cycloalkyl, alkenyl, alkenylaryl, aryl, arylalkyl, heteroaryl, acyl, alkoxy, cyano, carboxy, amino, hydroxyl, alkoxycarbonyl, nitro, alkylamino, dialkylamino and sulfo, and which are optionally substituted. Preferred substituents are as defined above.

Dipyrromethenboron difluoride dyes are generally soluble in organic solvents. Especially dipyrromethenboron difluoride dyes with aryl substituents are hydrophobic in nature and not soluble in aqueous solutions. Aqueous solubility however is usually required for bioanalytical applications. Hydrophilicity and solubility of a fluorescent label to aqueous solutions is often essential in terms of reducing unspecific binding, retaining photophysical properties of a label in labelled biomolecules and retaining biological properties of the labelled biomolecules. Aqueous solubility can be obtained by adding appropriate water-solubilizing groups to the basic chromophore. A water-solubilizing group preferably comprises ammonium or alkali metal salts of sulfonic or carboxylic acids, ammonium or hydroxyl groups. Aqueous solubility can also be obtained by adding a peptide or carbohydrate moiety to the dye.

According to this the preferred compounds of the present invention have a structure where the absorption and emission bands are appropriately tuned, the compound comprises a reactive side chain which can be used for covalent coupling of the compound to other molecules and the compound comprises also a group that increases solubility in aqueous solutions. According to this the preferred compounds of the present invention have the structure where at least one of the groups $R_1$, $R_2$, $R_3$, $R_4$, $R_5$, $R_6$ or $R_7$ is a substituted or unsubstituted phenyl, thienyl, pyrrolyl, furanyl, oxazolyl, isoxazolyl, oxadiazolyl, imidazolyl, benzoxazolyl, benzothiazolyl, benzimidazolyl, benzofuranyl, phenylethenyl or indolyl; and at least one of the groups $R_1$, $R_2$, $R_3$, $R_4$, $R_5$, $R_6$ or $R_7$ is substituted to yield a chemically reactive group that can be used for selective covalent linkage to other molecules and/or for further chemical modifications; and at least one of the groups $R_1$, $R_2$, $R_3$, $R_4$, $R_5$, $R_6$ or $R_7$ is substituted to yield a water-solubilizing group. According to this the most preferred compounds have the structure where $R_1$ is a substituted or unsubstituted phenyl, thienyl, pyrrolyl or phenylethenyl, $R_2$, $R_3$, $R_4$ and $R_5$ are each independently either hydrogen or alkyl, $R_6$ or $R_7$ is a substituent, which most preferably has the formula:

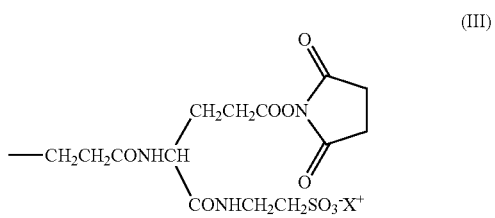

(III)

where $X^+$ is a cation, and the remaining substituent $R_6$ or $R_7$ is either hydrogen or alkyl. The preferred compounds of the present invention can also have the structure where the groups $R_1$, $R_2$, $R_3$, $R_5$, $R_6$ and $R_7$ are substituted or unsubstituted alkyl groups, $R_4$ is either hydrogen or substituted or unsubstituted alkyl; and at least one of the groups $R_1$, $R_2$, $R_3$, $R_4$, $R_5$, $R_6$ or $R_7$ is substituted to yield a chemically reactive group that can be used for selective covalent linkage to other molecules and/or for further chemical modifications; and at least one of the groups $R_1$, $R_2$, $R_3$, $R_4$, $R_5$, $R_6$ or $R_7$ is substituted to yield a water-solubilizing group. Preferred substituents are as defined above. Examples of two-photon fluorescent dipyrrometheneboron difluoride dyes that are water-soluble and thus especially suitable for labelling of biomolecules are presented in examples 3 and 8-17. These two-photon fluorescent dipyrro-metheneboron difluoride dyes are water-soluble and they have exceptionally low quenching by single pulse effect even under illumination with high two-photon excitation efficiency laser.

The two-photon fluorescent dipyrrometheneboron difluoride dyes according to present invention can be coupled with biospecific molecules yielding two-photon fluorescent conjugates. The biospecific molecule is a biologically active molecule, such as a hapten, biologically active ligand, drug, peptide, oligonucleotide, nucleotide, nucleic acid, polypeptide, protein, antibody, or a fragment of an antibody. The two-photon fluorescent conjugates can be used in a bioanalytical assay system where the specific signal is obtained via two-photon excited fluorescence of the said conjugate. The two-photon fluorescent dipyrromethene-boron difluoride dyes and conjugates according to present invention can also be used for staining of cells and tissues.

The following non-limiting examples are aimed to further demonstrate the invention. In the examples below, the compounds referred to (compounds 1 to 18) are disclosed in FIGS. 2a to 2h and 3.

EXAMPLE 1

3,3',5,5'-tetramethyl-4,4'-carboxyethyl-2,2'-dipyrrylmethene hydrobromide (1)

2-ethoxycarbonyl-3,5-dimethyl-4-methoxycarbonylethylpyrrole (1.0 g, 3.35 mmol) was dissolved in formic acid (3 ml) and hydrobromic acid (48%, 3 ml) was added. The reaction mixture was stirred at 100° C. for 2.5 h. After cooling the mixture to room temperature it was left to stand overnight at room temperature. The product crystallised out from the reaction mixture as small, orange, needle-like crystals. The reaction mixture was filtrated and the crystalline product was washed with water. The product, compound 1, was dried in vacuum desiccator. The yield was 677 mg (84%). Additional amount (43 mg) of product was obtained from the filtrate after 2 day standing at +4° C. The total yield was 720 mg (86%). 2-ethoxycarbonyl-3,5-dimethyl-4-methoxycarbonylethylpyrrole was prepared as described in Bullock E. et al., J. Chem. Soc. (1958) 1430.

EXAMPLE 2

4,4-difluoro-1,3,5,7-tetramethyl-4-bora-3a,4a diazasindacene-2,6-dipropionic Acid (2)

Dipyrrylmethene hydrobromide (compound 1) (500 mg, 1.17 mmol) was suspended in chloroform (20 ml) and triethylamine (4.3 ml, 31 mmol) was added. The starting dipyrrylmethene dissolved immediately after triethylamine addition (4.3 ml, 31 mmol). Boron trifluoride ethyletherate (5 ml, 31 mmol) was added. Reaction mixture was stirred at room temperature for 2.5 h. The reaction mixture was diluted with chloroform (50 ml), washed with dilute HCl (5%, 30 ml) and water (30 ml). Small amount (5%) ethanol was added in order to perform efficient extraction. Chloroform phase was evaporated to dryness in rotary evaporator and the product (compound 2) was precipitated from ethanol/water (7 days at +4° C.) yielding brown-orange powder. The yield after drying the product, compound 2, in vacuum desiccator was 420 mg (92%).

$^1$HNMR (JEOL JNM-LA400, DMSO-$d_6$, 400 MHz, δ ppm): 2.19 (s, 6H, 2x-$CH_3$), 2.29 (t, 4H, 2x-$CH_2$—), 2.38 (s, 6H, 2x-$CH_3$), 2.57 (t, 4H, 2x-$CH_2$), 7.53 (s, 1H, Ar—CH=).

EXAMPLE 3

4,4-difluoro-1,3,5,7-tetramethyl-6-carboxyethyl-4-bora-3a,4a-diaza-s-indacene-2-propionic acid succinimidylester (3)

4,4'-difluoro-1,3,5,7-tetramethyl-4-bora-3a,4a-diaza-s-indacene-2,6-dipropionic acid (compound 2) (102 mg, 0.26 mmol) was dissolved in N,N-dimethylformamide (2.5 ml, dry). N-hydroxysuccinimide (90 mg, 0.78 mmol) and N,N'-dicyclohexyl-carbodiimide (54 mg, 0.26 mmol) were added. Reaction mixture was stirred for 24 h at room temperature. N,N-dimethylformamide was evaporated (5 mbar, 40-50° C.) and the product was purified with column chromatography using silica as a stationary phase and dichloromethane:acetone:acetic acid (100:8:1, v:v:v) as an eluent. Fractions containing the desired mono-succinimidyl ester (compound 3) were combined and evaporated to dryness. The residue was dissolved into small amount of dichloromethane. Petroleum ether (bp 40-60° C.) was added to precipitate the product. The solution was filtrated and the precipitated product (compound 3) was obtained as an orange solid. Yield 50 mg (39%).

$^1$HNMR (JEOL JNM-LA400, DMSO-$d_6$, 400 MHz, δ ppm): 2.21 (s, 3H, $CH_3$), 2.22 (s, 3H, $CH_3$), 2.36 (t, 2H, —$CH_2$—), 2.40(s, 3H, $CH_3$), 2.41 (s, 3H, $CH_3$), 2.59 (t, 2H, —$CH_2$—), 2.72 (t, 2H, —$CH_2$—), 2.80 (s, 4H, 2x-$CH_2$—), 2.85 (t, 2H, —$CH_2$—), 7.60 (s, 1H, Ar—CH=)

UV-VIS (Ocean Ontics SD2000, MeOH): $\lambda_{max}$=523 nm (ϵ=91 000).

EXAMPLE 4

4,4-difluoro-5-(2-thienyl)-1,3-dimethyl-4-bora-3a,4a-diaza-s-indacene-2-propionic Acid Methyl Ester (4).

2-formyl-5-(2-thienyl)pyrrole (150 mg, 0.84 mmol) and 2,4-dimethyl-3-carboxy-ethylpyrrole (140 mg, 0.84 mmol) were dissolved in dichloromethane:methanol (10:1, 30 ml). Phosphorus oxychloride (77 µl, 0.84 mmol) was added and solution was stirred at room temperature for 18 h. Reaction mixture were evaporated to dryness and the residue was dissolved in dichloromethane (150 ml). N-ethyl-N,N-diisopropylamine (1.44 ml, 8.4 mmol) and boron trifluoride ethyl etherate (1.06 ml, 8.4 mmol) were added. Strong orange fluorescence was observed immediately after the addition of boron trifluoride ethyl etherate. The reaction mixture was washed with water, dried with sodium sulphate and evaporated to dryness. The crude product was purified with column chromatography using silica as a stationary phase and dichloromethane as an eluent. Fractions containing the desired product were pooled and evaporated to dryness yielding 304 mg (93%) of 4,4-difluoro-5-(2-thienyl)-1,3-dimethyl-4-bora-3a,4a-diaza-s-indacene-2-propionic acid methyl ester (compound 4).

$^1$HNMR (Bruker AM200, CDCl$_3$, 200 MHz, δ ppm): 2.21 (s, 3H, Ar—$CH_3$), 2.47 (t, 2H, —$CH_2$—), 2.59 (s, 3H, Ar—$CH_3$), 2.74 (t, 2H, —$CH_2$—), 3.68 (s, 3H, —$COOCH_3$), 6.70 (d, 1H, ArH), 6.91 (d, 1H, ArH), 7.05 (s, 1H, Ar—CH=), 7.15 (d, 1H, ArH), 7.40 (d, 1H, ArH), 8.04 (d, 1H, ArH). FAB-MS: MH$^+$389. UV-VIS (Ocean Optics SD2000, MeOH): $\lambda_{max}$=560 nm (ϵ=82 000).

2-(2-thienyl)pyrrole was prepared according to Kruse C. G. et al, *Heterocycles* 26 (1985) 3141 and formylated yielding 2-formyl-5-(2-thienyl)pyrrole according to Bullock E. et al. *J. Chem. Soc.* (1963) 2326 2,4-dimethyl-3-carboxyethylpyrrole was prepared as follows: 2-ethoxycarbonyl-3,5-dimethyl-4-methoxycarbonylethylpyrrole (1.5 g, 5.9 mmol) and potassium hydroxide (6.6 g) were dissolved in ethyleneglycol (50 ml). The reaction mixture was refluxed (190° C.) for 3 h under nitrogen atmosphere. Water (10 ml) was added and the mixture was refluxed for an additional 2 h. The cooled reaction mixture was diluted with water (200 ml), acidified with concentrated hydrochloric acid and extracted with diethylether. The organic extracts were pooled, dried with sodium sulphate and evaporated to dryness. The product was purified with column chromatography using silica as a stationary phase and dichloromethane:methanol (10:1, v:v) as an eluent. Fractions containing the product were pooled and evaporated to dryness yielding 720 mg (72%) of 2,4-dimethyl-3-carboxy-ethylpyrrole.

EXAMPLE 5

4,4-difluoro-5-(2-thienyl)-1,3-dimethyl-4-bora-3a,4a-diaza-s-indacene-2-propionic acid (5)

4,4-difluoro-5-(2-thienyl)-1,3-dimethyl-4-bora-3a,4a-diaza-s-indacene-2-propionic acid methyl ester (compound 4) (107 mg, 0.27 mmol) was dissolved in tetrahydro-furan:water (3:2, 50 ml). Phosphoric acid (85%, 3 ml) was added and the mixture was refluxed for 5 days. The reaction mixture was diluted with water and the product was extracted with dichloromethane. The organic phase was dried with sodium sulphate and evaporated to dryness. The crude product was purified with column chromatography using silica as a stationary phase and dichloro-methane:methanol (10:1) as an eluent. Fractions containing the desired product were pooled and evaporated to dryness. The product was crystallised from dichloromethane:petroleum ether yielding 68 mg (66%) of 4,4-difluoro-5-(2-thienyl)-1,3-dimethyl-4-bora-3a,4a-diaza-s-indacene-2-propionic acid (compound 5).

$^1$HNMR (Bruker AM200, DMSO-$d_6$, 200 MHz, δ ppm): 2.22 (s, 3H, Ar—$CH_3$), 2.40 (t, 2H, —$CH_2$—), 2.51 (s, 3H, Ar—$CH_3$), 2.63 (t, 2H, —$CH_2$—), 6.80 (d, 1H, ArH), 7.11 (d, 1H, ArH), 7.19 (dd, 1H, ArH), 7.69 (s, 1H, Ar—CH=), 7.73 (d, 1H, ArH), 7.88 (d, 1H, ArH).

EXAMPLE 6

4,4-difluoro-5-(2-thienyl)-1,3-dimethyl-4-bora-3a, 4a-diaza-s-indacene-2-propionic Acid Succinimidyl Ester (6).

4,4-difluoro-5-(2-thienyl)-1,3-dimethyl-4-bora-3 a,4a-diaza-s-indacene-2-propionic acid (compound 5) (57 mg, 0.15 mmol) was dissolved in anhydrous N,N-dimethyl-formamide (3 ml). N,N'-dicyclohexylcarbodiimide (47 mg, 0.23 mmol) and N-hydroxysuccinimide (52 mg, 0.45 mmol) were added and the mixture was stirred at room temperature for 20 h. Reaction mixture was diluted with dichloromethane and the precipitated N,N'-dicyclohexylurea was filtrated off. The filtrate was evaporated to dryness and the product was purified with column chromatography using silica as a stationary phase and dichloromethane:acetone:acetic acid (100:8:1, v:v: v) as an eluent. Fractions containing the product were combined and evaporated to dryness. The product was further dried in a vacuum desiccator yielding 35 mg (75%) of 4,4-difluoro-5-(2-thienyl)-1,3-dimethyl-4-bora-3a,4a-diaza-s-indacene-2-propionic acid succinimidyl ester (compound 6).
$^1$HNMR (Bruker AM200, CDCl$_3$, 200 MHz, δ ppm): 2.23(s, 3H, Ar—CH$_3$), 2.61 (s, 3H, Ar—CH$_3$), 2.74-2.82 (2 t, 4H, 2x-CH$_2$—), 2.86 (s, 4H, —CH$_2$—) 6.72 (d, 1H, ArH), 6.93 (d, 1H, ArH), 7.08 (s, 1H, Ar—CH=), 7.15 (dd, 1H, ArH), 7.41 (d, 1H, ArH), 8.06 (d, 1H, ArH)

EXAMPLE 7

Glu-Tau-Derivative of 4,4-difluoro-5-(2-thienyl)-1,3-dimethyl-4-bora-3a,4a-diaza-s-indacene-2-propionic Acid (7).

4,4-difluoro-5-(2-thienyl)-1,3-dimethyl-4-bora-3a,4a-diaza-s-indacene-2-propionic acid succinimidyl ester (compound 6) (35 mg, 0.074 mmol) and Glu-Tau-linker (compound 18) (19 mg, 0.074 mmol) was dissolved in anhydrous N,N-dimethyl-formamide (1 ml). Anhydrous triethylamine (31 μl, 0.22 mmol) was added and the reaction mixture was stirred at room temperature for 30 min. The reaction mixture was evaporated to dryness under reduced pressure. The crude product was used without further purification.
MS (Voyager DE-PRO, MALDI TOF, PerSeptive Biosystems, α-cyano-4-cinnamic acid matrix, negative mode): Calculated 609 (M−1), Found 609 (M−1)

EXAMPLE 8

Glu-Tau-succinimide derivative of 4,4-difluoro-5-(2-thienyl)-1,3-dimethyl-4-bora-3a,4a-diaza-s-indacene-2-propionic acid (8)

Glu-Tau-derivative of 4,4-difluoro-5-(2-thienyl)-1,3-dimethyl-4-bora-3a,4a-diaza-s-indacene-2-propionic acid (compound 7) (0.074 mmol) was dissolved in anhydrous N,N-dimethylformamide (2 ml). N,N'-dicyclohexylcarbodiimide (46 mg, 0.22 mmol) and N-hydroxysuccinimide (26 mg, 0.22 mmol) were added and the mixture was stirred at room temperature for 48 h. The precipitated N,N'-dicyclohexylurea was filtrated off and the filtrate was evaporated to dryness. The product was further dried in a vacuum desiccator and used without further purification.
MS (Voyager DE-PRO, MALDI TOF, PerSeptive Biosystems, α-cyano-4-cinnamic acid matrix, negative mode): Calculated 706 (M−1), Found 706 (M−1)

EXAMPLE 9

Glu-Tau-Succinimide Derivative of 4,4-difluoro-5-(2-pyrrolyl)-1,3-dimethyl-4-bora-3a,4a-diaza-s-indacene-2-propionic acid (9)

The Glu-Tau-succinimide derivative of 4,4-difluoro-5-(2-pyrrolyl)-1,3-dimethyl-4-bora-3a,4a-diaza-s-indacene-2-propionic acid, compound 9, was prepared with the same method as described in examples 7 and 8 using 4,4-difluoro-5-(pyrrolyl)-1,3-dimethyl-4-bora-3a,4a-diaza-s-indacene-2-propionic acid succinimidyl ester as a starting compound.
MS (Voyager DE-PRO, MALDI TOF, PerSeptive Biosystems, α-cyano-4-cinnamic acid matrix, negative mode): Calculated 689 (M−1), Found 689 (M−1)

EXAMPLE 10

Glu-Tau-Succinimide Derivative of 4,4-difluoro-5-phenyl-1,3-dimethyl-4-bora-3a,4a-diaza-s-indacene-2-propionic acid (10)

The Glu-Tau-succinimide derivative of 4,4-difluoro-5-phenyl-1,3-dimethyl-4-bora-3a,4a-diaza-s-indacene-2-propionic acid, compound 10, was prepared with the same method as described in examples 7 and 8 using 4,4-difluoro-5-phenyl-1,3-dimethyl-4-bora-3a,4a-diaza-s-indacene-2-propionic acid succinimidyl ester as a starting compound.
MS (Voyager DE-PRO, MALDI TOF, PerSeptive Biosystems, α-cyano-4-cinnamic acid matrix, negative mode): Calculated 700 (M−1), Found 700 (M−1)

EXAMPLE 11

Glu-Tau-Succinimide Derivative of 4,4-difluoro-5-(4-methoxyphenyl)-1,3-dimethyl-4-bora-3a,4a-diaza-s-indacene-2-propionic Acid (11)

The Glu-Tau-succinimide derivative of 4,4-difluoro-5-(4-methoxyphenyl)-1,3-di-methyl-4-bora-3a,4a-diaza-s-indacene-2-propionic acid, compound 11, was prepared with the same method as described in examples 7 and 8 using 4,4-difluoro-5(4-methoxyphenyl)-1,3-dimethyl-4-bora-3a,4a-diaza-s-indacene-2-propionic acid succinimidyl ester as a starting compound.
MS (Voyager DE-PRO, MALDI TOF, PerSeptive Biosystems, α-cyano-4-cinnamic acid matrix, negative mode): Calculated 730 (M−1), Found 730 (M−1)

EXAMPLE 12

Glu-Tau-Succinimide Derivative of 4,4-difluoro-5-styryl-1,3-dimethyl-4-bora-3a,4a-diaza-s-indacene-2-propionic Acid (12)

The Glu-Tau-succinimide derivative of 4,4-difluoro-5-styryl-1,3-dimethyl-4-bora-3a,4a-diaza-s-indacene-2-propionic acid, compound 12, was prepared with the same method as described in examples 7 and 8 using 4,4-difluoro-5-styryl-1,3-dimethyl-4-bora-3a,4a-diaza-s-indacene-2-propionic acid succinimidyl ester as a starting compound.
MS (Voyager DE-PRO, MALDI TOF, PerSeptive Biosystems, α-cyano-4-cinnamic acid matrix, negative mode): Calculated 726 (M−1), Found 726 (M−1)

EXAMPLE 13

Glu-Tau-Succinimide Derivative of 4,4-difluoro-5-(4-methoxystyryl)-1,3-dimethyl-4-bora-3a,4a-diaza-s-indacene-2-propionic Acid (13)

The Glu-Tau-succinimide derivative of 4,4-difluoro-5-(4-methoxystyryl)-1,3-dimethyl-4-bora-3a,4a-diaza-s-indacene-2-propionic acid, compound 13, was prepared with the same method as described in examples 7 and 8 using 4,4-difluoro-5-(4-methoxystyryl)-1,3-dimethyl-4-bora-3a, 4a-diaza-s-indacene-2-propionic acid succinimidyl ester as a starting compound.

MS (Voyager DE-PRO, MALDI TOF, PerSeptive Biosystems, α-cyano-4-cinnamic acid matrix, negative mode): Calculated 756 (M−1), Found 756 (M−1)

EXAMPLE 14

Glu-Tau-Amino Derivative of 4,4-difluoro-5-(2-thienyl)-1,3-dimethyl-4-bora-3a,4a-diaza-s-indacene-2-propionic Acid (14)

Glu-Tau-succinimide derivative of 4,4-difluoro-5-(2-thienyl)-1,3-dimethyl-4-bora-3a,4a-diaza-s-indacene-2-propionic acid (compound 8) (0.062 mmol) was dissolved in anhydrous N,N-dimethylformamide (3 ml). Triethylamine (26 µl, 0.185 mmol) and ethylenediamine (42 µl, 0.62 mmol) were added and the mixture was stirred at room temperature for 30 min. The reaction mixture was evaporated to dryness and the product was precipitated from dichloromethane-carbontetrachloride. The product, compound 14, was further dried in a vacuum desiccator and used without further purification.

MS (Voyager DE-PRO, MALDI TOF, PerSeptive Biosystems, α-cyano-4-cinnamic acid matrix, negative mode): Calculated 651 (M−1), Found 651 (M−1)

EXAMPLE 15

Glu-Tau-Arylamino Derivative of 4,4-difluoro-5-(2-thienyl)-1,3-dimethyl-4-bora-3a,4a-diaza-s-indacene-2-propionic acid (15)

Glu-Tau-succinimide derivative of 4,4-difluoro-5-(2-thienyl)-1,3-dimethyl-4-bora-3a,4a-diaza-s-indacene-2-propionic acid (compound 8) (0.074 mmol) was dissolved in anhydrous N,N-dimethylformamide (3 ml). Triethylamine (31 µl, 0.22 mmol) and 4-(2-aminoethyl)aniline (15 mg, 0.11 mmol) were added and the mixture was stirred at room temperature for 3 h. The reaction mixture was evaporated to dryness and the product was precipitated from dichloromethane/carbontetrachloride. The product, compound 15, was further dried in a vacuum desiccator and used without further purification.

MS (Voyager DE-PRO, MALDI TOF, PerSeptive Biosystems, α-cyano-4-cinnamic acid matrix, negative mode): Calculated 727 (M−1), Found 727 (M−1)

EXAMPLE 16

Glu-Tau-Isothiocyanato Derivative of 4,4-difluoro-5-(2-thienyl)-1,3-dimethyl-4-bora-3a,4a-diaza-s-indacene-2-propionic acid (16)

Glu-Tau-arylamino derivative of 4,4-difluoro-5-(2-thienyl)-1,3-dimethyl-4-bora-3a,4a-diaza-s-indacene-2-propionic acid (compound 15) (0.048 mmol) was dissolved in mixture of acetone (9 ml) and $NaHCO_3$ (9 ml, aq, saturated). Thiophosgene (183 µl, 2.4 mmol) was added and the mixture was stirred at room temperature for 1.5 h. The reaction mixture was diluted with water (50 ml) and dichloromethane (50 ml). The aqueous phase was washed twice with dichloromethane (40 ml). The product containing aqueous phase was extracted with phenol (2*20 ml). The product containing phenol phase was washed with water (40 ml) and diluted with diethylether (200 ml). The phenol/diethylether phase was extracted with water (4*30 ml) and the combined aqueous phase was washed twice with diethylether (30 ml). The product containing aqueous phase was evaporated to dryness and the product was precipitated from dichloromethane-carbontetrachloride. The product, compound 16, was further dried and stored in a vacuum desiccator.

MS (Voyager DE-PRO, MALDI TOF, PerSeptive Biosystems, α-cyano-4-cinnamic acid matrix, negative mode): Calculated 769 (M−1), Found 769 (M−1)

EXAMPLE 17

Glu-Tau-Maleimide Derivative of 4,4-difluoro-5-(2-thienyl)-1,3-dimethyl-4-bora-3a,4a-diaza-s-indacene-2-propionic acid (17)

Glu-Tau-amino derivative of 4,4-difluoro-5-(2-thienyl)-1,3-dimethyl-4-bora-3a,4a-diaza-s-indacene-2-propionic acid (compound 14) (0.015 mmol) was dissolved in anhydrous N,N-dimethylformamide (3 ml). Triethylamine (2.1 µl, 0.015 mmol) and N-succinimidyl 4-maleimidobutyrate (3.2 mg, 0.020 mmol) were added and the mixture was stirred at room temperature for 2 h. The reaction mixture was evaporated to dryness and the product was precipitated from dichloromethane/carbontetrachloride. The product, compound 17, was further dried and stored in a vacuum desiccator.

MS (Voyager DE-PRO, MALDI TOF, PerSeptive Biosystems, α-cyano-4-cinnamic acid matrix, negative mode): Calculated 816 (M−1), Found 816 (M−1)

EXAMPLE 18

Glu-Tau Linker (18)

A glutamic acid derivative, BOC-Glu(OtBu)-OSu (Nova Biochem, 500 mg, 1.25 mmol) was dissolved in anhydrous N,N-dimethylformamide (5 ml). To the solution of triethylamine (1.20 ml, 8.75 mmol) in water (10 ml) taurine (782 mg, 6.25 mmol) was dissolved. Taurine solution was added to the solution of BOC-Glu(OtBu)-OSu and the reaction mixture was stirred at room temperature for 30 min. Ethanol was added and the precipitated taurine was filtrated off and the filtrate was evaporated to dryness. The residue was dissolved in trifluoroacetic acid (2 ml) and stirred at room temperature for 2 h. The reaction mixture was evaporated to dryness and the residue was dissolved in dichloroethane:methanol. The product (compound 18) precipitated as a white solid upon slow evaporation of methanol in a rotary evaporator. The desired Glu-Tau linker (compound 18) was obtained in 64% yield (204 mg).

MS (ZABSpec-oaTOF, Fisons Instruments, glycerol matrix): Calculated 255 (M+1), Found 255 (M+1).

EXAMPLE 19

Measurements of Two-photon Fluorescence Yields of the Selected Two-photon Fluorescent Dyes Using a Laser with High Two-photon Excitation Efficiency The two-photon fluorescence yields were measured using experimental apparatus shown schematically in FIG. 5. Rhodamine B (Eastman Kodak) was selected as a reference because of its well-characterised fluorescence properties. Three dipyrromethenboron difluoride dyes named BODIPY 530/550, BODIPY 558/568 and BODIPY 564/576 as well as R-phycoerythrin (R-PE) were purchased from Molecular Probes. All organic dyes were dissolved in N,N-dimethylformamide and diluted with absolute ethanol to the concentration of 100 nM. The stock solution R-PE was diluted with phosphate buffered saline (50/150 mM, pH 7.4). The results are summarised in Table 1. The results are normalised to the signal of Rhodamine B (100). As it can be seen from the Table 1, the fluorescence yields of dipyrromethene boron difluoride dyes are in the same order as the fluorescence yield of Rhodamine B. The high fluorescence yields of dipyrromethene boron difluoride dyes make them an attractive alternative for Rhodamine type dyes. R-phycoerythrin has the highest fluorescence yield of the dyes presented here. However the applicability of the R-PE is limited because of the large size. The complexity of selective activation of the R-PE also limits its use as a label.

TABLE 1

Two-photon fluorescence yields of the selected two-photon fluorescent dyes

| Fluorescent dye | Normalised two-photon fluorescence yield [a.u.] |
|---|---|
| Dipyrromethene boron difluoride dyes | |
| Compound 3 | 18 |
| Compound 8 | 219 |
| BODIPY 530/550 | 66 |
| BODIPY 558/568 | 101 |
| BODIPY 564/576 | 128 |
| Rhodamine B | 100 |
| R-PE | 618 |

EXAMPLE 20

Labelling of Mouse IgG Anti-AFP With Two-photon Fluorescent dipyrromethene-boron Difluoride Dye 3

To the solution of 1.5 mg (9.3 nmol) of mouse IgG anti-AFP (clone A) in 400 μl phosphate buffered saline (10/150 mM, pH 7.4) 20 fold excess of compound 3 in anhydrous N,N-dimethylformamide (25 μl, c=7.5 mM) was added. 40 μl of NaHCO$_3$ (1 M, aq) was added and the mixture was incubated at room temperature for 2 h. The product was purified with NAP-5 gel filtration column (Amersham Pharmacia Biotech, Uppsala, Sweden) using phosphate buffered saline (50/150, 10 mM NaN$_3$, pH 7.4) as eluent. The fast moving orange fraction was collected and labelling degree was determined spectrophotometrically. Labelling degree of 5 fluorophores per protein was obtained.

EXAMPLE 21

Comparison of R-PE, Alexa 532 (Molecular Probes) and dipyrromethene boron difluoride Dye (3), in Microparticle Based Immunoassay The model assay is a separation free immunometric assay, utilising 3.1 μm amino-modified polystyrene microparticles (Amino Modified Microspheres PA05N, Bangs Laboratories, Inc., Fishers, Ind., U.S.A.) as solid phase. Mouse monoclonal anti-AFP IgG Fab' fragments (clone B) was covalently coupled to the microparticles by using a heterobifunctional ε-maleimidocaproyloxysuccinimide linker agent. The stock suspension of anti-AFP coated microparticles was diluted with TRIS pH 8.0 assay buffer to particle concentration of 0.05%. Mouse monoclonal IgG anti-AFP (clone A) was labelled with dipyrromethene boron difluoride dye (compound 3), Alexa 532 (Molecular Probes, Eugene, Oreg.) or with R-PE (Molecular Probes, Eugene, Oreg.) and used as a tracer. The tracers were diluted with an assay buffer to final concentration of 1.58 nM (compound 3), 1.45 nM (Alexa 532) and 0.78 nM (R-PE, Molecular Probes). 5 μl of microparticle suspension and 10 μl of tracer were mixed together with 10 μl of Alpha-1-Fetoprotein standards (X0900, Dako A/S, Denmark). The reaction mixtures was incubated for 2 hours in 37° C. and measured in the same reaction cuvette using experimental apparatus shown schematically in FIG. 5. The results are summarised in table 2 and in FIG. 4.

The tracer concentrations were optimised independently to each tracer. The dipyrromethene boron difluoride tracer gives the lowest background signal even though it was used in higher concentration than R-PE or Alexa 532 tracers. The assay background signal is important in terms of assay sensitivity. The most essential source of the background signal is the free fraction of labelled antibody (tracer) in the reaction suspension. The background levels of the three different tracers are presented in table 2 and in FIG. 4. These results clearly show that the best signal-to-background ratio is obtained with dipyrromethene boron difluoride labelled tracer. Moreover when comparing the assay results with the results of solution measurements (example 19, table 1) it can be seen that the two-photon fluorescence signal ratio between R-PE and compound 3 has changed dramatically. In solution measurement (table 1) the signal ratio of R-PE:compound 3 was 34 (618/18=34) in favour of R-PE whereas in particle measurement (table 2) the ratio was only 3.2 (25.6/8=3.2) in favour of R-PE.

TABLE 2

Two-photon fluorescence (TPF) signal measured from the surface of the microparticle in separation free AFP immunoassay. The signal of zero AFP concentration is originating mainly from the free tracer in the solution (= background signal)

| AFP concentration [ng/ml] | TPF signal (R-PE tracer) | TPF signal (Alexa 532 tracer) | TPF signal (compound 3 tracer) |
|---|---|---|---|
| 0 | 1.80 | 0.72 | 0.50 |
| 1 | 2.75 | 1.35 | 0.71 |
| 2 | 3.10 | 1.40 | 1.00 |
| 5 | 4.20 | 2.40 | 1.50 |
| 10 | 6.90 | 3.50 | 2.00 |
| 50 | 25.6 | 12.0 | 8.00 |
| 200 | 61.0 | 20.0 | 18.0 |
| 500 | 64.0 | 22.0 | 38.0 |

EXAMPLE 22

Measurements of Single Pulse Effect

The direct measurement of quenching by single pulse effect is difficult. It can be however measured indirectly by determining the axial resolution in the dye solution the depth component (z-response) is most prone to changes in resolution. The z-response was measured by using the instrument described in FIG. 5. The sample cuvette in FIG. 5 was replaced with a pair of microscope slides. The dye solutions were placed between these two microscope slides. As the dye solution sample was slowly moved to focus, a ramp of increasing signal was recorded. Maximum signal occurs when the focal volume overlaps the sample fully. The 20% to 80% fluorescence intensity distance was recorded for various dyes and is presented in table 3. The 20% to 80% fluorescence intensity distance values for dipyrromethene boron difluoride dyes are smaller than the same values for R-phycoerythrin or Rhodamine B. Thus, dipyrromethene boron difluoride dyes offer better spatial resolution and better signal-to-background ratio than rhodamines or R-PE in a two-photon excitation system with a laser with high two-photon excitation efficiency. This result is in good agreement with the result of microparticle measurement described in example 21.

TABLE 3

Two-photon 20% to 80% fluorescence intensity distance values of the selected two-photon fluorescent dyes.

| Fluorescent dye | 20% to 80% fluorescence intensity distance values [a.u.] |
|---|---|
| Dipyrrometheneboron difluoride dyes | |
| Compound 3 | 11.5 |
| Compound 8 | 12.6 |
| BODIPY 530/550 | 12.2 |
| BODIPY 558/568 | 13.7 |
| BODIPY 564/576 | 14.1 |
| Rhodamine B | 16.5 |
| R-PE | 21.5 |

EXAMPLE 23

Labelling of Oligonucleotides with Compound 6 and with Compound 8

To the solution of 5'-aminomodified oligonucleotide (17 bases, 28 μg, 5 nmol) in carbonate buffer (200 μl, 100 mM, pH 8.5) a 40 fold excess of labelling reagent (compound 6 or 8) in anhydrous DMF (50 μl) was added. Reaction mixture was incubated at 22° C. for 20 h. Labelled oligonucleotides were purified by using reverse phase HPLC (RP-18 column) and gradient elution technique. Solvents were A: 2% acetonitrile in triethylammonium acetate buffer (50 mM, pH 7) and B: 70% acetonitrile in triethylammonium acetate buffer (50 mM, pH 7). The gradient was started from 5% of solvent B and the amount of solvent B linearly raised to 40% in 25 minutes. Both dye-oligonucleotide conjugates (labelled with compound 6 or with compound 8) eluted between 18 to 22 minutes while the unlabelled oligonucleotide eluted at a time point of 10 minutes. The unbound labelling reagent was removed from the column by increasing the amount of solvent B to 100%.

The concentrations of the labelled oligonucleotides were determined spectrophotometrically. A labelling yield of 25% (compound 6) and 20% (compound 8) was obtained. The labelled oligonucleotides were diluted to equimolar concentrations and the fluorescence yields were determined both by one- and two-photon excitation techniques. As a result the fluorescence yield of oligonucleotide labelled with compound 8 was found to be one order of magnitude higher compared to the oligonucleotide labelled with compound 6. The same result was obtained both by one- and two-photon excitation techniques. The higher fluorescence yield of oligonucleotide labelled with compound 8 can be explained with increased hydrophilicity of the label compound and increased distance between the label and the oligonucleotide.

EXAMPLE 24

Labelling of Mouse IgG Anti-AFP with Fluorescent dipyrrometheneboron difluoride Dyes (6 and 8).

To the solution of 0.2 mg (1.25 nmol) of mouse IgG anti-AFP (clone A) in 40 μl phosphate buffered saline (10/150 mM, pH 7.4) a 5 fold excess (6.25 nmol) of compound 6 or compound 8 in anhydrous N,N-dimethylformamide was added. 4 μl of NaHCO$_3$ (1 M, aq) was added and the mixture was incubated at room temperature for 3 h. The products were purified with NAP-5 gel filtration column (Amersham Pharmacia Biotech, Uppsala, Sweden) using phosphate buffered saline (50/150, 10 mM NaN$_3$, pH 7.4) as eluent. The fast moving coloured fractions were collected. The labelling degrees of these protein conjugates (compound 6 and 8) were determined spectrophotometrically. Labelling degrees of 2.3 (compound 6) and 2.5 (compound 8) fluorophores per protein were obtained.

EXAMPLE 25

Comparison of Antibody Tracers Labelled With Compound 6 and Compound 8 in Microparticle Based Immunoassay The AFP assay was performed by using 3.2 μm carboxy modified polystyrene microparticles (Carboxy Modified Microspheres PC05N, Bangs Laboratories, Inc., Fishers, Ind., U.S.A.) as solid phase. Mouse monoclonal anti-AFP IgG (clone B) was covalently coupled to the microparticles by using EDAC (1-ethyl-3-(dimethyl-aminopropyl)carbodiimide) coupling method (TechNote #205, Bangs Laboratories, Inc., Fishers, Ind., U.S.A.). The stock suspension of anti-AFP coated microparticles was diluted with TRIS pH 8.0 assay buffer to particle concentration of $1.5 \cdot 10^7$ particles/ml. Mouse monoclonal IgG anti-AFP (clone A) was labelled with dipyrrometheneboron difluoride dye (compound 6 or 8) and used as a tracer. The tracers were diluted with an assay buffer to concentration of 16 nM. 5 μl of micorparticle suspension and 5 μl of tracer were mixed together with 10 μl of Alpha-1-Fetoprotein standards (X0900, Dako A/S, Denmark). The reaction mixture was incubated for 2 hours in 37° C. and measured in the same reaction cuvette using experimental apparatus shown schematically in FIG. 5. The results are summarised in tables 4 and 5.

TABLE 4

AFP immunoassay using tracer labelled with compound 6. All concentration points were measured from six parallel samples.

| AFP concentration [ng/ml] | 2PF-signal (average of 6 parallel measurements) | Standard deviation SD | Coefficient of variation (%) CV | Signal-background (S-S0) |
|---|---|---|---|---|
| 0 | 6.03 | 9.03 | 149.66 | 0.00 |
| 0.1 | 3.02 | 0.67 | 22.26 | −3.01 |
| 1 | 6.63 | 5.14 | 77.46 | 0.60 |
| 5 | 12.74 | 3.28 | 25.71 | 6.71 |
| 10 | 18.18 | 3.63 | 19.96 | 12.15 |
| 20 | 45.01 | 7.83 | 17.40 | 38.98 |
| 100 | 141.46 | 23.13 | 16.35 | 135.43 |
| 400 | 249.48 | 27.66 | 11.09 | 243.45 |
| 1000 | 260.98 | 31.94 | 12.24 | 254.95 |

The sensitivity of an assay is often determined by calculating the standard deviation (SD) of the signal from parallel samples at zero analyte concentration. The lowest concentration of analyte that gives greater signal than 3SD (standard deviation at zero analyte concentration multiplied by factor 3) is generally used for assigning the sensitivity of an assay.

The sensitivity of the assay is greatly affected by background signal (signal to background ratio) as described in example 21 and by repeatability of the measurement.

TABLE 5

AFP immunoassay using tracer labelled with compound 8.
All concentration points were measured from six parallel samples.

| AFP concentration [ng/ml] | 2PF-signal (average of 6 parallel measurements) | Standard deviation SD | Coefficient of variation (%) CV | Signal-background (S-S0) |
|---|---|---|---|---|
| 0 | 5.11 | 0.28 | 5.46 | 0.00 |
| 0.1 | 5.88 | 0.26 | 4.47 | 0.77 |
| 1 | 7.05 | 0.35 | 5.00 | 1.94 |
| 5 | 13.36 | 0.79 | 5.95 | 8.25 |
| 10 | 20.65 | 1.52 | 7.38 | 15.54 |
| 20 | 39.37 | 3.80 | 9.66 | 34.26 |
| 100 | 140.33 | 20.25 | 14.43 | 135.23 |
| 400 | 274.69 | 16.79 | 6.11 | 269.58 |
| 1000 | 333.22 | 12.45 | 3.74 | 328.12 |

The results presented in tables 4 and 5 clearly show that the tracer labelled with the hydrophilic dipyrrometheneboron difluoride dye (compound 8) provides more sensitive assay. The difference in 3SD values between the two tracers is surprisingly large, more than an order of magnitude (3SD Compound 8=0.84 vs. 3SD Compound 6=27). This means that the tracer labelled with the hydrophilic dipyrrometheneboron difluoride dye (compound 8) provides an order of magnitude better assay sensitivity than the tracer labelled with the hydrophobic dipyrrometheneboron difluoride dye (compound 6). In average, both the tracers give response that is dependent on the analyte concentration while the tracer with hydrophilic dipyrrometheneboron difluoride dye (compound 8) exhibit somewhat higher signal level. In addition, the tracer labelled with the hydrophilic dipyrrometheneboron difluoride dye (compound 8) provides remarkably smaller signal variation (coefficient of variation) throughout the assay range in comparison to the tracer labelled with the hydrophobic dye (compound 6).

It will be appreciated that the methods of the present invention can be incorporated in the form of a variety of embodiments, only a few of which are disclosed herein. It will be apparent for the specialist in the field that other embodiments exist and do not depart from the spirit of the invention. Thus, the described embodiments are illustrative and should not be construed as restrictive.

The invention claimed is:

1. A separation free bioanalytical assay method for measuring an analyte from a biological fluid or suspension comprising providing a bioaffinity binding solid phase comprising a suspension of microparticles coated with a biospecific primary reagent, adding a biospecific secondary reagent labeled with a two-photon fluorescent dipyrrometheneboron difluoride dye, adding a biological fluid or suspension comprising an analyte to the suspension of microparticles, thereby forming a reaction suspension, focusing a laser into the reaction suspension to illuminate the two-photon fourescent dipyrrometheneboron difluoride dye in a focal volume, and measuring two-photon excited fluorescence from single microparticles when they randomly float or are guided by the radiation pressure of the excitation laser through the focal volume of the laser beam, wherein said two-photon fluorescent dipyrrometheneboron difluoride dye has a structure (II),

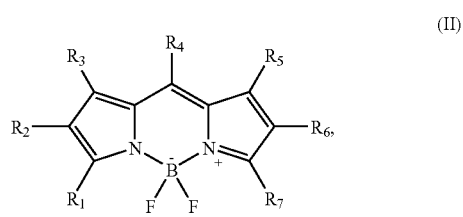

(II)

wherein $R_1$ is substituted or unsubstituted 2-thienyl, 2-pyrrolyl, phenyl or phenylethenyl and at least one of the groups $R_2$, $R_3$, $R_4$, $R_5$, $R_6$ or $R_7$ is

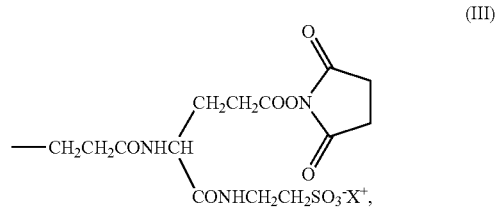

(III)

where $X^+$ is a cation; and the remaining groups of $R_2$, $R_3$, $R_4$, $R_5$, $R_6$ and $R_7$ are each independently of each other either hydrogen or alkyl.

2. The assay method of claim 1, wherein said biospecific secondary reagent is a biologically active molecule selected from the group consisting of a hapten, biologically active ligand, drug, peptide, oligonucleotide, nucleotide, nucleic acid, polypeptide, protein, antibody and fragment of antibody.

3. The assay method according of claim 1, wherein said analyte is a biologically active molecule selected from the group consisting of a hapten, biologically active ligand, drug, peptide, oligonucleotide, nucleotide, nucleic acid, polypeptide, protein, antibody, and a fragment of an antibody.

* * * * *